(12) United States Patent
Long et al.

(10) Patent No.: US 9,169,258 B2
(45) Date of Patent: Oct. 27, 2015

(54) DORIPENEM INTERMEDIATE COMPOUND, PREPARATION PROCESS THEREFOR AND USE THEREOF, AND PREPARATION PROCESS FOR DORIPENEM

(71) Applicant: SHENZHEN HAIBIN PHARMACEUTICAL CO., LTD., Shenzhen, Guangdong (CN)

(72) Inventors: Lisong Long, Shenzhen (CN); Zhaoqiang Lu, Shenzhen (CN); Cheng Ding, Shenzhen (CN); Guangcheng Li, Shenzhen (CN); Zhili Lv, Shenzhen (CN); Congquan Wu, Shenzhen (CN); Yanjun Zhang, Shenzhen (CN); Peng Ren, Shenzhen (CN)

(73) Assignee: Shenzhen Haibin Pharmaceutical Co., Ltd., Guangdong (CN)

( * ) Notice: Subject to any disclaimer, the term of this patent is extended or adjusted under 35 U.S.C. 154(b) by 0 days.

(21) Appl. No.: 14/387,829

(22) PCT Filed: Sep. 26, 2012

(86) PCT No.: PCT/CN2012/082054
§ 371 (c)(1),
(2) Date: Sep. 24, 2014

(87) PCT Pub. No.: WO2013/143266
PCT Pub. Date: Oct. 3, 2013

(65) Prior Publication Data
US 2015/0038700 A1 Feb. 5, 2015

(30) Foreign Application Priority Data
Mar. 26, 2012 (CN) .......... 2012 1 0082240

(51) Int. Cl.
*C07D 477/20* (2006.01)
*C07D 477/06* (2006.01)
*C07D 477/08* (2006.01)

(52) U.S. Cl.
CPC ............ *C07D 477/20* (2013.01); *C07D 477/06* (2013.01); *C07D 477/08* (2013.01)

(58) Field of Classification Search
CPC .............................. C07D 477/06; C07D 477/20

USPC .......................................................... 540/350
See application file for complete search history.

(56) References Cited

FOREIGN PATENT DOCUMENTS

| CH | 102285988 | * 12/2011 |
| CN | 1071428 A | 4/1993 |
| CN | 101613351 A | 12/2009 |
| WO | WO 2010/097686 | * 9/2010 |

OTHER PUBLICATIONS

Zhang et al., "Synthesis, of Doripenem," Chinese Journal of Pharmaceuticals, 37(6), 2006, (English translation included), 4 pages.

* cited by examiner

*Primary Examiner* — Taofiq A Solola
(74) *Attorney, Agent, or Firm* — Christie, Parker & Hale, LLP.

(57) ABSTRACT

The present invention provides a doripenem intermediate compound shown by formula (XIV), wherein PNB is p-nitrobenzyl, and HX is an acid; and when HX is a monobasic acid, n=1; and when HX is a polybasic acid, n=2. The present invention also provides a process for preparing the doripenem intermediate compound (XIV). In addition, the present invention provides a process for preparing doripenem (I) from the doripenem intermediate compound (XIV) in a simple manner, with a high yield and low production costs. The new mono-protected doripenem intermediate compound provided in the present invention contains only one protecting group, reducing the difficulty and complexity in the subsequent deprotection step by catalytic hydrogenation, increasing the yield of the catalytic hydrogenation reaction, and thus reducing the production cost of the final product. The process is easy to operate and suitable for industrialized production.

(XIV)

$$\left( \begin{array}{c} \text{structure with OH, SO}_2\text{NH}_2, \text{COOPNB, NH groups} \end{array} \right)_n \cdot HX \cdot H_2O$$

31 Claims, 4 Drawing Sheets

DORIPENEM INTERMEDIATE COMPOUND, PREPARATION PROCESS THEREFOR AND USE THEREOF, AND PREPARATION PROCESS FOR DORIPENEM

CROSS-REFERENCE TO RELATED APPLICATIONS

This application is a National Phase Patent Application and claims priority to and benefit of International Application Number PCT/CN2012/082054, filed on Sep. 26, 2012, which claims priority to and benefit of Chinese Patent Application Number 201210082240.1, filed on Mar. 26, 2012, the entire disclosures of which are incorporated herein by reference.

TECHNICAL FIELD

The present invention relates to a doripenem intermediate and a process for preparing the same, as well as a process for preparing doripenem from the intermediate.

BACKGROUND ART

The antibiotics of carbapenems represented by imipenem, meropenem, and biapenem, etc., have characteristics of broad-spectrum and super-strong antibacterial activity, β-lactamase stability and low toxicity, etc., which make them have become one of the most important antibacterial drugs for the treatment of severe bacterial infections.

Doripenem, with chemical name of (+)-(4R,5S,6S)-6-[(1R)-1-hydroxyethyl]-4-methyl 7-oxo-3-[[(3S,5S)-5-[(aminosulfonylamino)-methyl]-3-pyrrolidinyl]thio]-1-azabicyclo[3.2.0]hept-2-ene-2-carboxylic acid, and structure shown in formula (I), is researched and developed by Japanese Shionogi & Co., Ltd, and came to market for the first time in Japan in 2005 under the trade name of "Finibax", it belongs to antibiotics of 1-β methyl-type carbapenems, with broad-spectrum antibacterial activity. In recent years, various methods for preparing doripenem have been developed, in these methods, doripenem is usually prepared by reacting the parent nucleus compound (II) of carbapenem antibiotic compounds with the side-chain compound (III) of doripenem to obtain the intermediate compound (IV), and then removing the protecting group through catalytic hydrogenation, the reaction process is as follows:

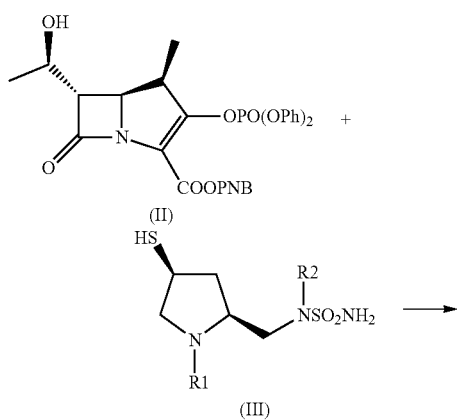

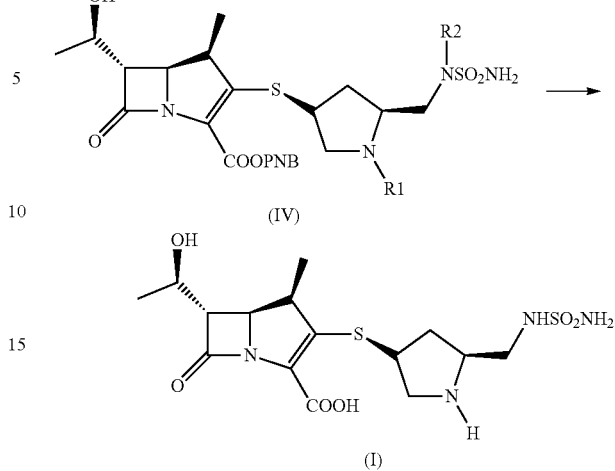

(PNB = p-O$_2$NC$_6$H$_4$CH$_2$)

According to the above reaction route, *Organic Process Research & Development* 2003, 7, 846-850 reported the following method for preparing doripenem (I):

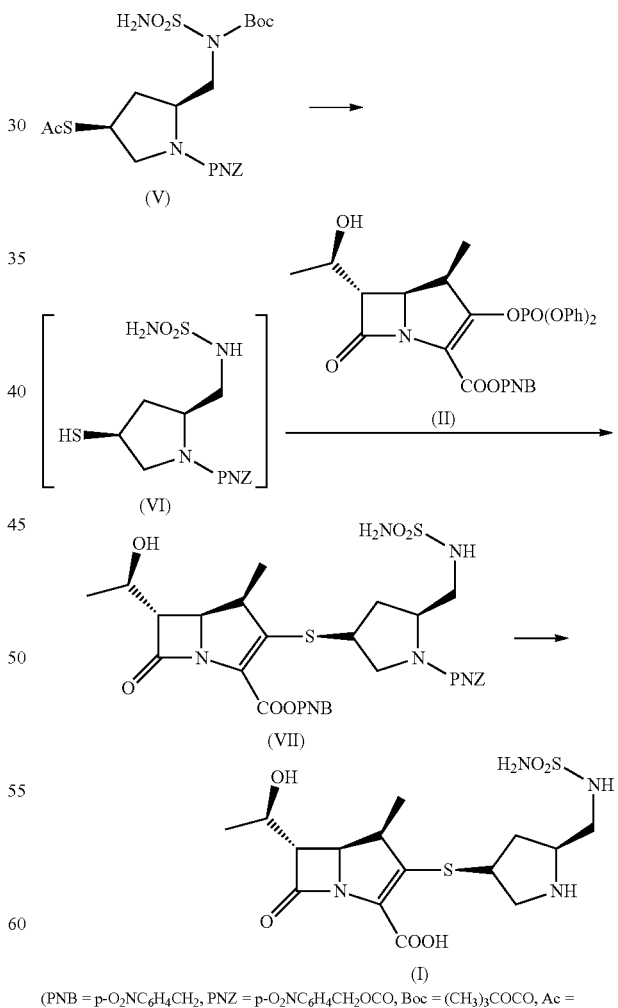

(PNB = p-O$_2$NC$_6$H$_4$CH$_2$, PNZ = p-O$_2$NC$_6$H$_4$CH$_2$OCO, Boc = (CH$_3$)$_3$COCO, Ac = CH$_3$CO)

In this method, the doubly-protected doripenem intermediate compound (VII) is prepared with yield of 88%, however, the intermediate compound (VII) is an amorphous foamy solid which is not easy to be purified and stored, while the purity of the intermediate compound (VII) has great impact on the subsequent step where de-protection is performed by catalytic hydrogenation (the yield of the subsequent step where doripenem (I) is obtained by removing protecting groups through catalytic hydrogenation is only 73%), therefore, this method is not a preferred method for industrial production of doripenem (I).

Patent EP0528678 reported a method for preparing doripenem by purifying the intermediate compound (VII) through column chromatography and then performing de-protection through catalytic hydrogenation. Although purification of the intermediate compound (VII) through column chromatography improves the yield of the subsequent step where the protecting groups are removed by catalytic hydrogenation (doripenem (I) can be obtained with yield of 84.8% by removing the protecting groups of the purified intermediate compound (VII) through catalytic hydrogenation), but the step of isolating and purifying the intermediate compound (VII) through column chromatography undoubtedly increases the production costs of doripenem and reduces the production efficiency, therefore, this method is also not a preferred method for industrial production of doripenem (I).

In order to overcome the difficulty in purification of the doubly-protected doripenem intermediate compound (VII), Patent CN101613351 reported a method for isolating and purifying the intermediate compound (VII). In this method, the methanol solvate crystal (VIII) of the doripenem intermediate compound (VII) is obtained from the doubly-protected doripenem intermediate compound (VII) under the specified condition (adding methanol successively into the solution of the intermediate compound (VII)):

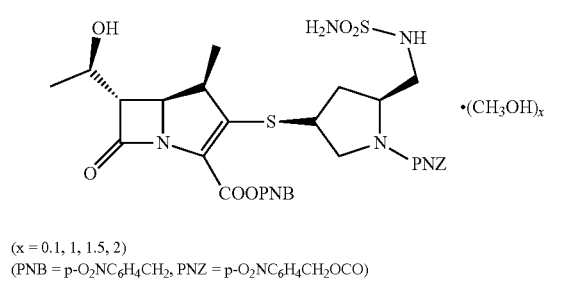

(x = 0.1, 1, 1.5, 2)
(PNB = p-O₂NC₆H₄CH₂, PNZ = p-O₂NC₆H₄CH₂OCO)

Although the doubly-protected doripenem intermediate compound crystal (VIII) with a purity of above 98% can be obtained by this method at a certain yield (the maximum yield is 87%), which provides convenience for the purification of the intermediate compound (VII), this method needs a long operation time (it requires to stir for 8 hours to achieve yield of 87%), reducing the production efficiency, therefore, the method is still not a preferred method for industrial production of doripenem (I).

Patent WO2007009354 reported a method for preparing doripenem (I) by the route shown below:

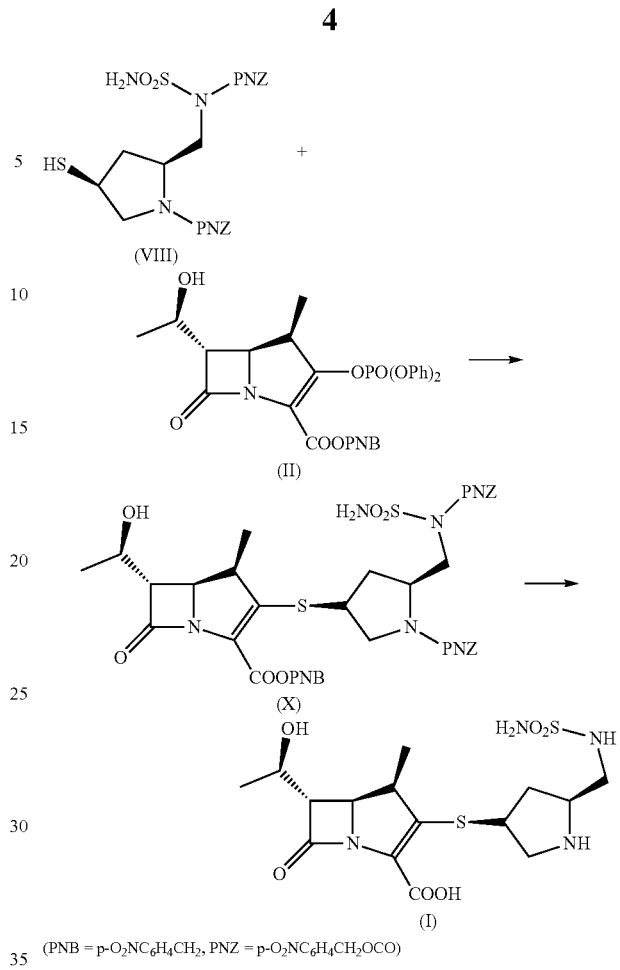

(PNB = p-O₂NC₆H₄CH₂, PNZ = p-O₂NC₆H₄CH₂OCO)

In this method, a tri-protected doripenem intermediate compound (X) is firstly prepared, then doripenem (I) is prepared by de-protection reaction where catalytic hydrogenation is performed. Although this method avoids the step of removing protecting groups in the side-chain compound, this brings difficulties in the subsequent step where de-protection is performed by catalytic hydrogenation since the resulting intermediate compound (X) is an amorphous foamy solid which is not easy to be purified and stored; in addition, the intermediate compound (X) contains three protecting groups, increasing the complexity of de-protection by catalytic hydrogenation. The above two aspects result in low yield (49%) of the subsequent step where de-protection is performed by catalytic hydrogenation, therefore this method is not a preferred method for industrial production of doripenem (I).

In addition to the above three methods, *Chinese Journal of Pharmaceuticals* (2006, volume 37, No 6, Pages 361-363) also reported a method for preparing doripenem (I) by the route shown below:

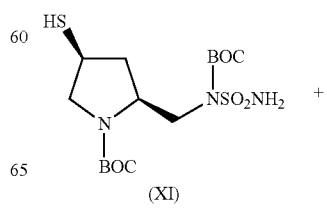

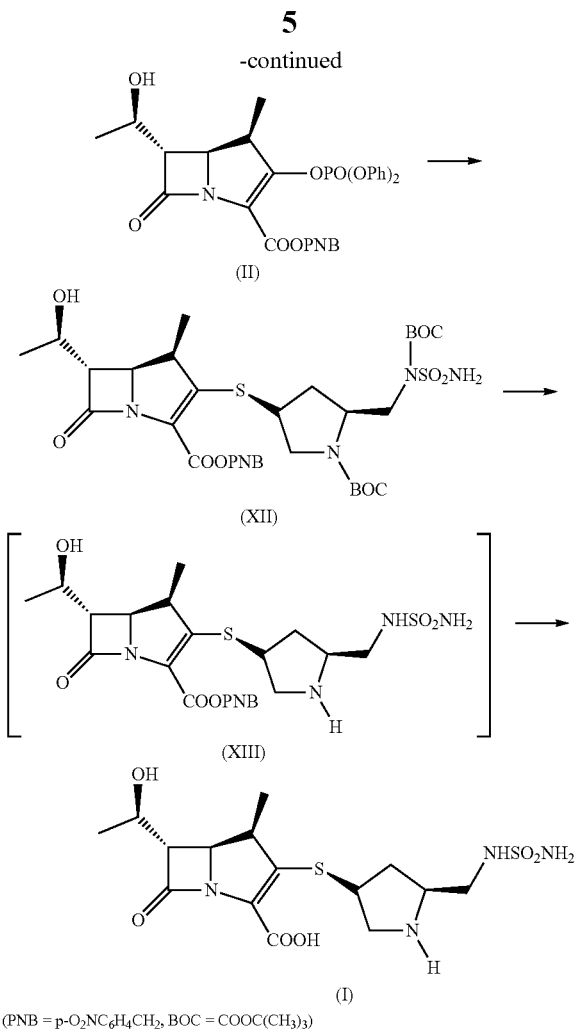

(PNB = p-O$_2$NC$_6$H$_4$CH$_2$, BOC = COOC(CH$_3$)$_3$)

In this method, as the protecting group of the side-chain compound (XI) is not consistent with that of the parent nucleus compound (II), the protecting groups of the doripenem intermediate compound (XII) are respectively removed with different methods in twice, which undoubtedly increases the reaction steps, reduces the use efficiency of the parent nucleus compound (II) and increases the production costs.

Further, since the doripenem intermediate compound (XIII) is directly subjected to de-protection by catalytic hydrogenation without purification, resulting in a low yield (58.1%) of the subsequent step where de-protection is performed by catalytic hydrogenation, therefore, this method is also not a preferred method for industrial production of doripenem (I).

Summarizing the above four methods, it can be seen that the protected doripenem intermediate compounds (such as intermediate compounds (VII), (X) and (XIII)) prepared by the existing preparation methods are not easy to be purified and stored, which brings many difficulties in the subsequent step where de-protection is performed by catalytic hydrogenation; additionally, the multiple protecting groups (such as intermediate compounds (VII) and (X)) also increase the complexity and difficulty in the subsequent step where de-protection is performed by catalytic hydrogenation, reduce the yield of the step where de-protection is performed by catalytic hydrogenation and increase the production costs, therefore, it is particularly important and urgent to find a protected doripenem intermediate compound which is easy to implement industrial production and purification and a more efficient method for de-protection by catalytic hydrogenation.

SUMMARY OF THE INVENTION

One object of the present invention is to provide a doripenem intermediate compound (XIV) which is easy to be produced and purified industrially.

Another object of the present invention is to provide a process for preparing the doripenem intermediate compound (XIV).

The third object of the present invention is to provide a process for preparing doripenem (I) from the doripenem intermediate compound (XIV) in a simple manner, with a high yield and low production costs.

The technical solutions of the present invention are as follows.

In one aspect, the present invention provides a doripenem intermediate compound represented by formula (XIV),

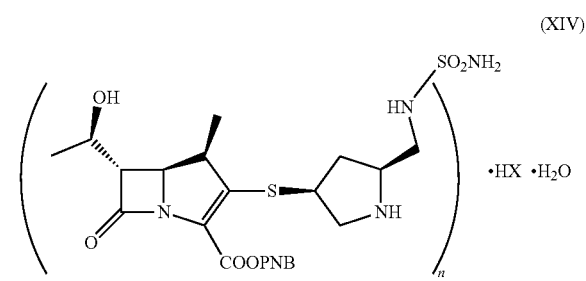

wherein, PNB is p-nitrobenzyl, and HX is an acid; and when HX is a monobasic acid, n=1; and when HX is a polybasic acid, n=2.

According to the acid-alkali proton theory, the acid can be divided into a monobasic acid (e.g. HCl, NH$_4^+$), dibasic acid (e.g. H$_2$C$_2$O$_4$, H$_2$SO$_4$) and tribasic acid (e.g. H$_3$PO$_4$) and so on based on the number of the protons (H$^+$) which the acid can donate. In the present invention, the non-monobasic acid is referred to as polybasic acid. The monobasic acid and polybasic acid may either be an inorganic acid or organic acid.

The present inventors found that, when HX is a monobasic acid, n=1; and when HX is a dibasic acid, n=2, however, when HX is a polybasic acid (such as tribasic acid) which can donate more than two protons (H$^+$), n is still 2, which will not increase with the increasing of number of the donated protons (H$^+$). This may be related to steric hindrance, or may be related to the fact that the acidity of the third proton after two protons (H$^+$) are donated by the polybasic acid is too weak so that the proton cannot be donated.

Preferably, HX is an inorganic or organic acid;

Preferably, HX is selected from hydrochloric acid, hydrobromic acid, nitric acid, acetic acid, formic acid, propionic acid, n-butyric acid, isobutyric acid, trichloroacetic acid, benzoic acid, salicylic acid, lactic acid, sulfuric acid, phosphoric acid, phosphorous acid, oxalic acid, maleic acid, succinic acid, fumaric acid, malic acid, tartaric acid, citric acid;

Further preferably, HX is hydrochloric acid, sulfuric acid, phosphoric acid or acetic acid. When HX is hydrochloric acid or acetic acid, n=1; and when HX is sulfuric acid or phosphoric acid, n=2.

Preferably, the doripenem intermediate compound represented by formula (XIV) is a crystal.

Further preferably, the present invention provides a crystal of the doripenem intermediate compound (XIV), wherein HX is hydrochloric acid, n=1. Under radiation of Cu-Kα rays, the X-ray diffraction pattern of the crystal comprises the diffraction peaks at the following angles of 2θ: 14.05±0.2°, 17.25±0.2°, 21.65±0.2°, 22.60±0.2°, 31.80±0.2°, 45.60±0.2°; preferably, the X-ray diffraction pattern of the crystal further comprises the diffraction peaks at the following angles of 2θ: 9.40±0.2°, 27.45±0.2°.

The present invention further provides a crystal of another doripenem intermediate compound (XIV), wherein HX is sulfuric acid, n=2. Under radiation of Cu-Kα rays, the X-ray diffraction pattern of the crystal comprises the diffraction peaks at the following angles of 2θ: 14.05±0.2°, 17.20±0.2°, 21.20±0.2°, 21.65±0.2°, 22.50±0.2°, 45.55±0.2°; preferably, the X-ray diffraction pattern of the crystal further comprises a diffraction peak at the following angle of 2θ: 12.90±0.2°

The present invention further provides a crystal of yet another doripenem intermediate compound (XIV), wherein HX is acetic acid, n=1. Under radiation of Cu-Kα rays, the X-ray diffraction pattern of the crystal comprises the diffraction peaks at the following angles of 2θ: 13.45±0.2°, 17.45±0.2°, 21.20±0.2°, 22.55±0.2°, 25.15±0.2°, 45.60±0.2°; preferably, the X-ray diffraction pattern of the crystal further comprises the diffraction peaks at the following angles of 2θ: 8.85±0.2°, 24.15±0.2°, 27.45±0.2°, 33.95±0.2°.

The present invention further provides a crystal of still another doripenem intermediate compound (XIV), wherein HX is phosphoric acid, n=2. Under radiation of Cu-Kα rays, the X-ray diffraction pattern of the crystal comprises the diffraction peaks at the following angles of 2θ: 14.10±0.2°, 17.15±0.2°, 18.90±0.2°, 19.25±0.2°, 21.55±0.2°; preferably, the X-ray diffraction pattern of the crystal further comprises the diffraction peaks at the following angles of 2θ: 12.90±0.2°, 24.80±0.2°.

The above angles of 2θ are obtained by selecting the main peaks with relative strong intensity in the X-ray diffraction pattern, but the structure of the crystal is not necessarily be limited by these values, that is, the structure of the crystal may contain other peaks besides the peaks mentioned above. In addition, the crystal is generally analyzed and measured by X-rays, some measurement errors may be produced in the peak of the crystal due to the presence of the measurement instrument, measurement conditions and adhered solvents, etc. For example, the angle of 2θ may produce measurement error of about ±0.2°, therefore, when the structure of the crystal is identified, some errors should be considered, the crystals with characteristics of the X-ray pattern substantially identical to the above X-ray pattern are all within the scope of the present invention.

In another aspect, the present invention provides a process for preparing the doripenem intermediate compound, the process comprises the following steps:

(1-1) subjecting a parent nucleus compound (II) of carbapenem antibiotic compounds and a side-chain compound (XV) of doripenem to a condensation reaction in an organic solvent under the action of a base;

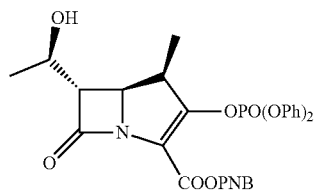

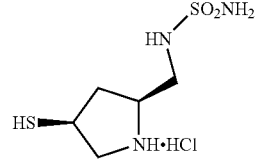

and (1-2) reacting the reaction mixture or product obtained in the step (1-1) with the water solution containing HX to obtain the doripenem intermediate compound represented by formula (XIV),

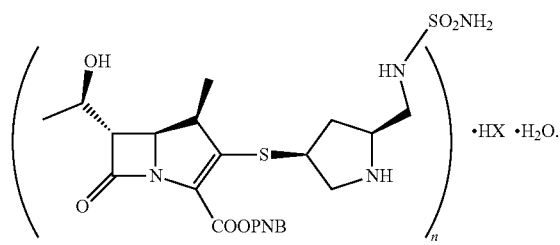

In the formula (XIV), PNB is p-nitrobenzyl, and HX is an acid; and when HX is a monobasic acid, n=1; when HX is a polybasic acid, n=2.

Preferably, HX is selected from hydrochloric acid, hydrobromic acid, nitric acid, acetic acid, formic acid, propionic acid, n-butyric acid, isobutyric acid, trichloroacetic acid, benzoic acid, salicylic acid, lactic acid, sulfuric acid, phosphoric acid, phosphorous acid, oxalic acid, maleic acid, succinic acid, fumaric acid, malic acid, tartaric acid, citric acid.

Wherein the organic solvent in the step (1-1) is selected from one or more of acetonitrile, N,N-dimethylformamide, N,N-dimethylacetamide, N,N-diethylformamide and N,N-diethylacetamide, and preferably N,N-dimethylformamide and/or acetonitrile;

preferably, the base in the step (1-1) is an organic base, and preferably selected from one or more of triethylamine, N,N-diisopropylethylamine, tetramethyl guanidine and tri-n-butylamine, and preferably triethylamine and/or N,N-diisopropylethylamine;

preferably, in the step (1-1), the reaction temperature is −60~15° C., preferably −35~−15° C.;

preferably, in the step (1-1), the molar ratio of the parent nucleus compound (II) of carbapenem antibiotic compounds, the side-chain compound (XV) of doripenem to the organic base is 1:1~2:1~3, preferably 1:1.2:2.5;

preferably, in the step (1-1), the reaction concentration calculated based on the parent nucleus compound (II) may be 0.01~2 mol/L, preferably 0.2 mol/L;

preferably, in the step (1-1), the reaction time is 3~24 hours, preferably 3-5 hours.

Preferably, in the step (1-2), the molar ratio of HX to the parent nucleus compound (II) in the step (1-1) is 1~10:1, preferably 5~6:1; the weight percent concentration of the water solution containing HX is 0.01%~1%, preferably 0.5%~1%;

In the step (1-2), the reaction temperature is −15~40° C., preferably 0~10° C.; and reaction time is 3~36 hours, preferably 5~6 hours.

Preferably, after the step (1-2), the process further comprises the following steps:

(1-3) adding an organic solvent, stirring and washing to perform purification;

preferably, the organic solvent is selected from one or more of methanol, ethanol, tetrahydrofuran, isopropanol, acetonitrile, N,N-dimethylformamide, N,N-dimethylacetamide, N,N-diethylformamide, N,N-diethylacetamide, acetone, methyl acetate, ethyl acetate, dichloromethane, methyl tert-butyl ether, chloroform and toluene;

preferably, the volume of the organic solvent is 1~10 times, preferably 1~3 times the volume of the organic solvent used in the step (1-1).

In the third aspect, the present invention provides a use of the doripenem intermediate compound in the preparation of doripenem. The doripenem intermediate compound of the present invention is a mono-protected doripenem intermediate, and can be a crystalline solid, therefore it can be directly and conveniently used to the preparation of doripenem.

In the fourth aspect, the present invention provides a method for preparing doripenem represented by formula (I), the method comprises: preparing doripenem represented by formula (I) in a solvent under the action of a catalyst by using the doripenem intermediate compound according to any one of claims 1-4 through de-protection reaction where the catalytic hydrogenation is performed,

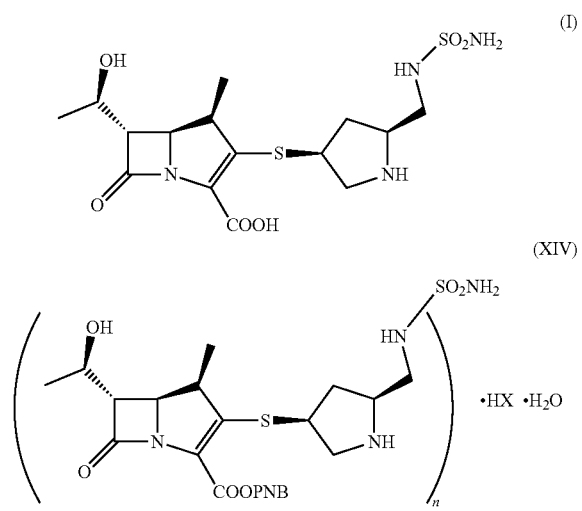

wherein, PNB is p-nitrobenzyl, and HX is an acid; and when HX is a monobasic acid, n=1; and when HX is a polybasic acid, n=2.

Preferably, HX is selected from hydrochloric acid, hydrobromic acid, nitric acid, acetic acid, formic acid, propionic acid, n-butyric acid, isobutyric acid, trichloroacetic acid, benzoic acid, salicylic acid, lactic acid, sulfuric acid, phosphoric acid, phosphorous acid, oxalic acid, maleic acid, succinic acid, fumaric acid, malic acid, tartaric acid, citric acid.

Further preferably, HX is hydrochloric acid, sulfuric acid, phosphoric acid or acetic acid; when HX is hydrochloric acid or acetic acid, n=1; when HX is sulfuric acid or phosphoric acid, n=2.

Preferably, the doripenem intermediate compound (XIV) is a crystal.

Preferably, in the de-protection reaction by catalytic hydrogenation, the solvent is a mixed solvent of organic solvent/water; further preferably, the organic solvent is selected from one or more of methanol, tetrahydrofuran, ethanol, N,N-dimethylformamide, acetone and isopropanol;

more preferably, the solvent is a mixed solvent of tetrahydrofuran/water; preferably, the volume of tetrahydrofuran, the volume of water and the mass of the doripenem intermediate compound (XIV) are in a ratio of 10~100 ml:10~100 ml:1 g, preferably 15 ml:15 ml:1 g;

preferably, in the de-protection reaction by catalytic hydrogenation, the catalyst is selected from one or more of Pd/C, Pd(OH)$_2$/C, Pt/C and Raney Ni, and preferably Pd/C; further preferably, the mass ratio of Pd/C to the mono-protected doripenem intermediate compound (XIV) is 0.05~2:1, preferably 0.25:1;

preferably, the de-protection reaction by catalytic hydrogenation is performed at a hydrogen pressure of 1~40 atm, more preferably at a hydrogen pressure of 20~30 atm;

preferably, the de-protection reaction by catalytic hydrogenation is performed at a temperature of 0~45° C., preferably at a temperature of 20~30° C.;

preferably, the de-protection reaction by catalytic hydrogenation is performed at a pH of 4~9, further preferably at a pH of 6.5~7.5. Wherein the pH is preferably adjusted by a buffer system, the buffer system is selected from one or more of N-methyl morpholine/acetic acid, N-methyl morpholine/hydrochloric acid, N-methyl morpholine/formic acid, 2,6-dimethylpyridine, 3-morpholinopropanesulfonic acid/sodium hydroxide, sodium bicarbonate, morpholine/acetic acid, morpholine/hydrochloric acid, morpholine/formic acid, potassium dihydrogen phosphate/dipotassium hydrogen phosphate, and preferably N-methyl morpholine/acetic acid and/or 2,6-dimethylpyridine; wherein, when the pH is adjusted by N-methyl morpholine/acetic acid, the volume of N-methyl morpholine, the volume of acetic acid and the mass of the mono-protected doripenem intermediate compound (XIV) are in a ratio of 1~5 ml:0.05-2 ml:1 g, preferably in a ratio of 1 ml:0.25 ml:1 g; or when the pH is adjusted by 2,6-dimethylpyridine, the volume of 2,6-dimethylpyridine and the mass of the doripenem intermediate compound (XIV) are in a ratio of 0.05~1 ml:1 g, preferably in a ratio of 0.33 ml:1 g.

Preferably, the above process further comprises:

after the de-protection reaction by catalytic hydrogenation finishes, adding a water-miscible organic solvent to the obtained hydrogenated solution to precipitate a crystal of doripenem (I).

Wherein, the organic solvent is selected from one or more of methanol, isopropanol, acetone, N,N-dimethylformamide, ethanol, tetrahydrofuran, and preferably methanol/isopropanol and/or acetone/isopropanol; further preferably, the methanol/isopropanol is used as a solvent for crystallization, the volume of methanol, the volume of isopropanol and the mass of the doripenem intermediate compound (XIV) are in a ratio of 30~100 ml:100-300 ml:1 g, preferably 60 ml:225 ml:1 g; or acetone/isopropanol is used as a solvent for crystallization, and the volume of methanol, the volume of isopropanol and the mass of the doripenem intermediate compound (XIV) are in a ratio of 20~100 ml:100-300 ml:1 g, preferably in a ratio of 60 ml:225 ml:1 g.

Preferably, the crystallization temperature of doripenem (I) is −15~5° C., preferably −5~5° C.

According to embodiments of the present invention, the present invention provides a process for preparing doripenem represented by formula (I),

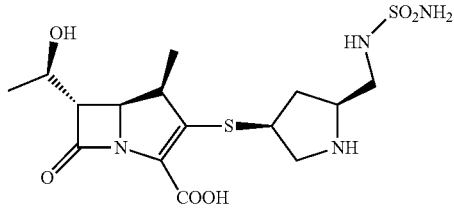

wherein, PNB is p-nitrobenzyl, and HX is an acid; and when HX is a monobasic acid, n=1; and when HX is a polybasic acid, n=2.

Preferably, HX is selected from hydrochloric acid, hydrobromic acid, nitric acid, acetic acid, formic acid, propionic acid, n-butyric acid, isobutyric acid, trichloroacetic acid, benzoic acid, salicylic acid, lactic acid, sulfuric acid, phosphoric acid, phosphorous acid, oxalic acid, maleic acid, succinic acid, fumaric acid, malic acid, tartaric acid, citric acid.

Further preferably, HX is hydrochloric acid, sulfuric acid, phosphoric acid or acetic acid. When HX is hydrochloric acid or acetic acid, n=1; when HX is sulfuric acid or phosphoric acid, n=2.

Preferably, the doripenem intermediate compound (XIV) is a crystal.

The process comprises the following steps:

(1-1) subjecting a parent nucleus compound (II) of carbapenem antibiotic compounds and a side-chain compound (XV) of doripenem to a condensation reaction in an organic solvent under the action of a base,

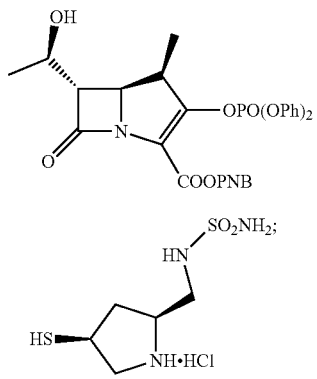

(1-2) reacting the reaction mixture or product obtained in the step (1-1) with the water solution containing HX to obtain a doripenem intermediate compound represented by formula (XIV),

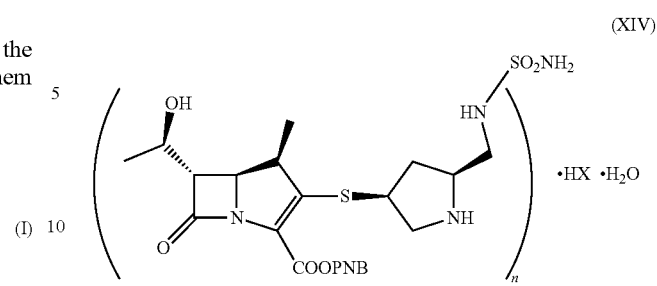

(1-3) adding optionally an organic solvent, stirring and washing to perform purification; and (2) preparing the doripenem represented by formula (I) in a solvent under the action of a catalyst by subjecting the doripenem intermediate compound represented by formula (XIV) to a de-protection reaction where the catalytic hydrogenation is performed.

The technical solutions of the present invention are described in detail below.

According to embodiments of the present invention, the structure and preparation process of the doripenem intermediate compound (XIV) provided by the present invention and the process for preparing doripenem (I) from the intermediate compound are as follows:

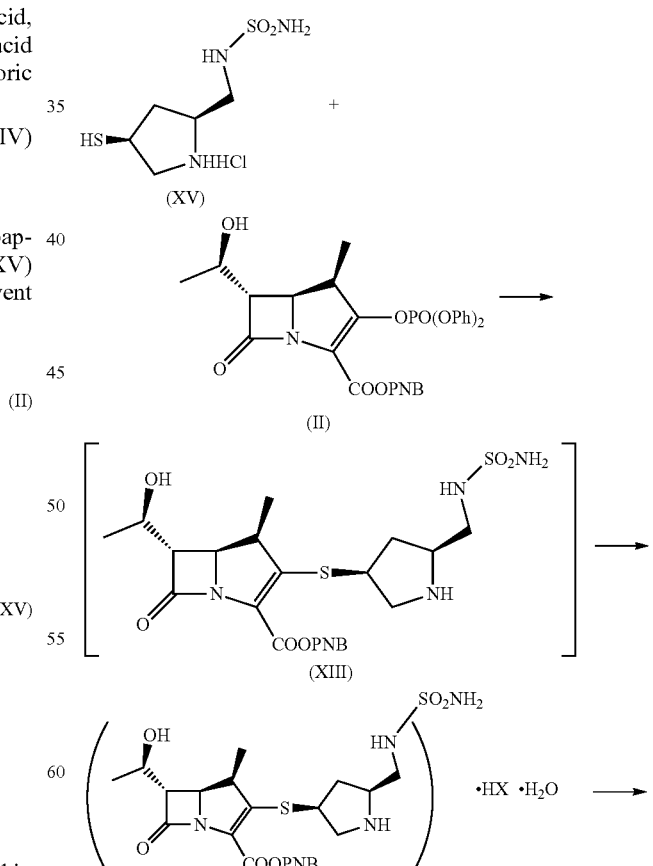

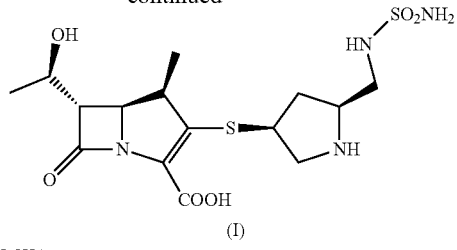

(PNB = p-O₂NC₆H₄CH₂)

when HX is a monobasic acid, n=1; and when HX is a polybasic acid, n=2.

Preferably, when the monobasic acid is selected from hydrochloric acid, hydrobromic acid, nitric acid, acetic acid, formic acid, propionic acid, n-butyric acid, isobutyric acid, trichloroacetic acid, benzoic acid, salicylic acid, lactic acid, n is 1; when the polybasic acid is selected from sulfuric acid, phosphoric acid, phosphorous acid, oxalic acid, maleic acid, succinic acid, fumaric acid, malic acid, tartaric acid, citric acid, n is 2.

More preferably, HX is hydrochloric acid, sulfuric acid, phosphoric acid or acetic acid; when HX is hydrochloric acid or acetic acid, n=1; when HX is sulfuric acid or phosphoric acid, n=2.

Preferably, the doripenem intermediate compounds (XIV-a~w) are crystals.

In the preparation process of the present invention, doripenem (I) is prepared from the parent nucleus compound (II) via two steps of reaction:

1, subjecting the parent nucleus compound (II) and the side-chain compound (XV) of doripenem to a condensation reaction under the action of a base, then reacting the resulting reaction mixture or product with the water solution containing HX, and performing isolation to obtain the mono-protected doripenem intermediate compound (XIV-a~w); or the process further comprises the purification step of adding an organic solvent, stirring and washing, so as to obtain the mono-protected high-purity crystalline doripenem intermediate compound (XIV-a~w);

2, preparing doripenem represented by formula (I) by subjecting the resulting mono-protected doripenem intermediate compound (XIV-a~w) to a de-protection reaction where the catalytic hydrogenation is performed.

In the step 1, the adopted organic solvent is selected from acetonitrile, N,N-dimethylformamide, N,N-dimethylacetamide, N,N-diethylformamide, N,N-diethylacetamide, and preferably selected from N,N-dimethylformamide and acetonitrile; the reaction concentration calculated based on the parent nucleus compound (II) may be 0.01~2 mol/L, preferably 0.2 mol/L; the organic base is selected from triethylamine, N,N-diisopropylethylamine, tetramethyl guanidine, tri-n-butylamine, preferably selected from triethylamine and N,N-diisopropylethylamine; the reaction temperature may be −60~15° C., preferably −35~−15° C.; the molar ratio of the parent nucleus compound (II) of carbapenem antibiotic compounds, side-chain compound (XV) of doripenem to the organic base is 1:1~2:1~3, preferably 1:1.2:2.5; and the reaction time is 3~24 hours, preferably 3~5 hours. After completion of the reaction, the resulting reaction mixture is poured into the water solution containing acid (HX) to react, then isolation is performed to obtain the mono-protected doripenem intermediate compound (XIV-a~w). The adopted acid is an organic acid or inorganic acid, and may be a monobasic acid or polybasic acid, and is selected from hydrochloric acid, sulfuric acid, phosphoric acid, nitric acid, acetic acid, formic acid, propionic acid, n-butyric acid, isobutyric acid, oxalic acid, maleic acid, succinic acid, fumaric acid, lactic acid, malic acid, tartaric acid, citric acid, gluconic acid, benzoic acid, benzenesulfonic acid, methanesulfonic acid, trichloroacetic acid, salicylic acid, the inorganic acid is preferably hydrochloric acid, sulfuric acid and phosphoric acid, and the organic acid is preferably acetic acid. When the adopted acid is hydrochloric acid and acetic acid, n=1; when the adopted acid is sulfuric acid and phosphoric acid, n=2; and the molar ratio of the acid to the parent nucleus compound (II) is 1~10:1, preferably 5~6:1; the weight percent concentration of the acid aqueous solution is 0.01%~1%, preferably 0.5%~1%; or the purification step of adding an organic solvent, stirring and washing is further included; the organic solvent is selected from methanol, ethanol, tetrahydrofuran, isopropanol, acetonitrile, N,N-dimethylformamide, N,N-dimethylacetamide, N,N-diethylformamide, N,N-diethylacetamide, acetone, methyl acetate, ethyl acetate, dichloromethane, methyl tert-butyl ether, chloroform, toluene; wherein the organic solvent is preferably selected from ethyl acetate and dichloromethane; and the volume of the organic solvent is 1~10 times, preferably 1~3 times the volume of the solvent used for reacting the parent nucleus compound (II) with the side-chain compound (XV) of doripenem; the reaction temperature of forming a salt by reacting the reaction mixture of the parent nucleus compound (II) and the side-chain compound (XV) of doripenem with the acid aqueous solution is −15~40° C., preferably 0~10° C.; and the reaction time is 3~36 hours, preferably 5~6 hours.

Preferably, the organic solvent is further added, and stirring, isolating and washing are performed to obtain the mono-protected high-purity crystalline doripenem intermediate compound (XIV-a~w), and then the step 2 is performed.

In the step 2, the used solvent is a mixed solvent of organic solvent/water. Further preferably, the organic solvent is selected from methanol, tetrahydrofuran, ethanol, N,N-dimethylformamide, acetone, isopropanol, and preferably a mixed solvent of tetrahydrofuran/water; further preferably, the volume of tetrahydrofuran, the volume of water and the mass of the mono-protected doripenem intermediate compound (XIV-a~w) are in a ratio of 10~100 ml:10~100 ml:1 g, preferably in a ratio of 15 ml:15 ml:1 g; the pH range for the hydrogenation reaction is 4~9, preferably 6.5~7.5; the used buffer system is N-methyl morpholine/acetic acid, N-methyl morpholine/hydrochloric acid, N-methyl morpholine/formic acid, 2,6-dimethylpyridine, 3-morpholinopropanesulfonic acid/sodium hydroxide, sodium bicarbonate, morpholine/acetic acid, morpholine/hydrochloric acid, morpholine/formic acid, potassium dihydrogen phosphate/dipotassium hydrogen phosphate, and preferably N-methyl morpholine/acetic acid and 2,6-dimethyl pyridine; when N-methyl morpholine/acetic acid is used as a buffer, the volume of N-methyl morpholine, the volume of acetic acid and the mass of the mono-protected doripenem intermediate compound (XIV-a~w) are in a ratio of 1~5:0.05~2:1, preferably in a ratio of 1:0.25:1; when 2,6-dimethylpyridine is used as a buffer, the volume of 2,6-dimethylpyridine and the mass of the mono-protected doripenem intermediate compound (XIV-a~w) are in a ratio of 0.05~1 ml:1 g, preferably in a ratio of 0.33 ml:1 g; the catalyst used for the hydrogenation reaction is selected from Pd/C, Pd(OH)₂/C, Pt/C, Raney Ni, preferably Pd/C; further preferably, the mass ratio of Pd/C to the mono-protected doripenem intermediate compound (XIV-a~w) is 0.05~2:1, preferably 0.25:1; the hydrogen pressure in the hydrogenation reaction is 1~40 atm, preferably 20~30 atm; preferably, the de-protection reaction by catalytic hydrogenation is performed at a temperature of 0~45° C., preferably at a temperature of 20~30° C.; after completion of the hydrogenation reaction, a water-miscible organic solvent is added to the hydrogenated solution to precipitate the crystal of doripenem (I). The added organic solvent is selected from methanol, isopropanol, acetone, N,N-dimethylformamide, ethanol, tetrahydrofuran, or mixed solvents consisting of two or more of the above solvents, and is preferably methanol/isopropanol and acetone/isopropanol; further preferably, when methanol/isopropanol is used as a crystallization solvent, the volume of methanol, the volume of isopropanol and the mass of the mono-protected doripenem intermediate compound (XIV-a~w) are in a ratio of 30~100 ml:100~300 ml:1 g, preferably in a ratio of 60 ml:225 ml:1 g; and when acetone/isopropanol is used as a crystallization solvent, the volume of methanol, the volume of isopropanol and the mass of the mono-protected doripenem intermediate compound (XIV-a~w) are in a ratio of 20~100 ml:100~300 ml:1 g, preferably in a ratio of 60 ml:225 ml:1 g; the crystallization temperature of doripenem (I) is −15~5° C., preferably −5~5° C.

Most of the protected doripenem intermediate compounds provided in the prior art are amorphous foamy solids, which are not easy to be purified and stored, while their purities have great impact on the subsequent step where de-protection is performed by catalytic hydrogenation; further, the protected doripenem intermediate compound provided in the prior art usually contain two or more protecting groups, which will undoubtedly increase the difficulty and complexity in the subsequent step where de-protection is performed by catalytic hydrogenation, thereby reducing the yield of the catalytic hydrogenation reaction and increasing the production cost of the final product. Compared with the prior art, the technical solutions provided by the present invention have the following technical effects:

first, the novel doripenem intermediate compound provided by the present invention is a mono-protected doripenem intermediate compound, which only contains one protecting group, reducing the difficulty and complexity in the subsequent step where the de-protection is performed by catalytic hydrogenation, and thereby improving the yield of the catalytic hydrogenation reaction and reducing the production costs of the final product;

Second, different from the protected side-chain intermediate compounds of doripenem in the prior art, which are usually foamy solids, the novel mono-protected doripenem intermediate compound provided in the present invention is crystalline solid, therefore it is easily purified and stored, and has low production cost and short production cycle, and can be used directly and conveniently; the mono-protected high-purity doripenem intermediate compound ensures the high yield of the subsequent step where the de-protection is performed by catalytic hydrogenation and the high quality of the final product;

thirdly, the process for preparing and purifying the novel mono-protected doripenem intermediate compound and the subsequent process of de-protection by catalytic hydrogenation and the process for crystallization of the final product provided in the present invention have advantages of simple operation and so on, which are suitable for factory large-scale applications.

BRIEF DESCRIPTION OF THE DRAWINGS

Hereinafter, the embodiments of the present invention will be illustrated in detail in combination with the accompanying drawings, wherein.

DETAILED DESCRIPTION OF THE EMBODIMENTS

The present invention will be further described in detail in conjunction with the specific embodiments, and the examples provided are only intended to illustrate the present invention rather than limit the scope of the present invention.

The side-chain compound (XV) of doripenem can be prepared by referring to Chinese Patent No. 201110239140.0; the parent nucleus compound (II) can be purchased commercially or synthesized by referring to U.S. Pat. No. 4,933,333.

The experimental methods in the following examples are all conventional methods unless expressly stated. The experimental materials such as medicinal materials and reagent materials used in the following examples are all purchased commercially unless expressly stated.

EXAMPLE 1

Synthesis of Compound (XIV-a)

Under the protection of nitrogen, 11.88 g (20 mmol) compound (II) and 5.94 g (24 mmol) compound(XV) were dissolved in 100 ml N,N-dimethylformamide, cooled to −15~−25° C., and added slowly with 6.37 g (50 mmol) N,N-diisopropylethylamine, and then stirred for 5 hours after the completion of addition, then the reaction finished; the reaction mixture was added into 500 ml hydrochloric acid solution with weight percent concentration of 0.5%, stirred at 0° C. for 30 minutes, and add with 100 ml methylene chloride and stirred for 5 hours with the temperature controlled below 10° C., and then filtered and dried, then 10.9 g white crystalline solid compound (XIV-a) was obtained with yield of 91.8%.

(+)-(4R,5S,6S)-6-[(1R)-1-hydroxyethyl]-4-methyl-7-oxo-3-[[(3S,5S)-5-[(aminosulfonylamino)-methyl]-3-pyrrolidinyl]thio]-1-azabicyclo[3.2.0]hept-2-ene-2-carboxylic acid p-nitrobenzyl ester hydrochloride (XIV-a):

HPLC shows that the compound (XIV-a) has a purity of 99% and moisture of 3.9%;

m/z: 556 [(M−HCl)+H]$^+$, $^1$H NMR (300 MHz, DMSO-d$_6$): δ 1.2 (m, 6H), 1.6 (m, 1H), 3.1 (m, 1H), 3.3 (m, 3H), 3.5 (m, 1H), 3.7 (m, 2H), 4.0 (m, 2H), 4.3 (d, 1H), 5.2 (d, 1H), 5.3 (d, 1H), 5.4 (d, 1H), 6.8 (s, 2H), 7.0 (t, 1H), 7.7 (d, 2H), 8.2 (d, 2H);

Elemental analysis: calculated: $C_{22}H_{32}ClN_6O_9S_2$, C, 43.31%; H, 5.29%; N, 11.48%; S, 10.51%. Measured: C, 44.00%; H, 5.14%; N, 10.98%; S, 9.88%.

The chemical structural formula of the compound (XIV-a) is as follows:

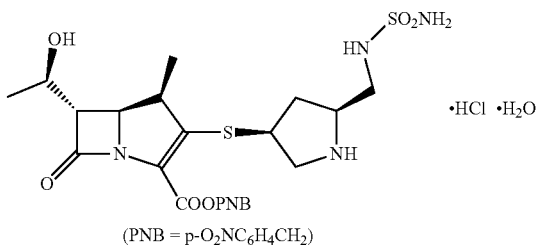

(XIV-a)

(PNB = p-O$_2$NC$_6$H$_4$CH$_2$)

Figure 1:
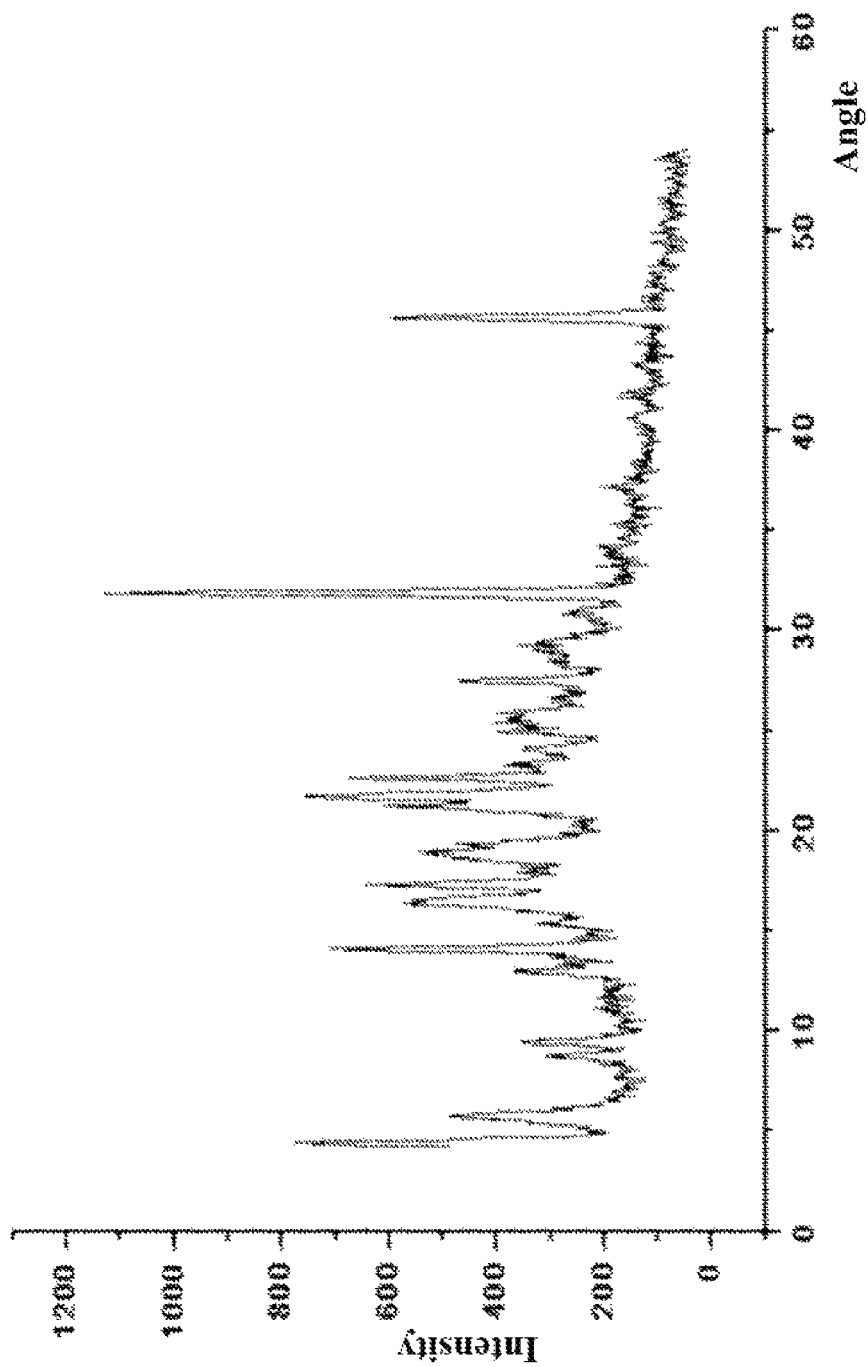
FIG. 1 shows X-ray powder diffraction pattern of the crystal of the compound represented by formula (XIV-a) prepared in Example 1.

The X-ray diffraction pattern of the compound (XIV-a) crystal is shown in FIG. 1, and the specific testing conditions and results are shown in Table 1.

Testing instrument: Innov-X systems BTX-219 X-ray diffractometer.

Testing conditions: target: Cu; 2θ scan at the beginning: 3.000; 2θ scan at the end: 60.000; voltage: 30 KV; current: 330 μA; Ka1=1.54060, Ka2=1.54433, Ka2/Ka1=0.5, Ka=1.54184.

TABLE 1

X-ray diffraction pattern data of the compound (XIV-a)

| NOs | Angles of 2θ | d (Angstrom) values | Intensity countings | Intensities (%) |
|---|---|---|---|---|
| 1 | 9.40 | 9.4009 | 234 | 23.8 |
| 2 | 14.05 | 6.2983 | 550 | 56.0 |
| 3 | 17.25 | 5.1365 | 446 | 45.4 |
| 4 | 21.65 | 4.1015 | 537 | 54.6 |
| 5 | 22.60 | 3.9312 | 457 | 46.6 |
| 6 | 27.45 | 3.2466 | 253 | 25.8 |
| 7 | 31.80 | 2.8117 | 982 | 100.0 |
| 8 | 45.60 | 1.9878 | 527 | 53.6 |

EXAMPLE 2

Synthesis of Compound (XIV-b)

Under the protection of nitrogen, 11.88 g (20 mmol) compound (II) and 5.94 g (24 mmol) compound(XV) were dissolved in 100 ml acetonitrile, cooled to −15~−25° C., and added slowly with 5.06 g (50 mmol) triethylamine, and then stirred for 5 hours after the completion of addition, then the reaction finished; the reaction mixture was added into 500 ml sulfuric acid solution with weight percent concentration of 0.5%, stirred at 0° C. for 30 minutes, and add with 300 ml ethyl acetate and stirred for 3 hours with the temperature controlled below 10° C., and then filtered and dried, then 11.2 g white crystalline solid compound (XIV-b) was obtained with yield of 93%.

(+)-(4R,5S,6S)-6-[(1R)-1-hydroxyethyl]-4-methyl-7-oxo-3-[[(3S,5S)-5-[(aminosulfonylamino)-methyl]-3-pyrrolidinyl]thio]-1-azabicyclo[3.2.0]hept-2-ene-2-carboxylic acid p-nitrobenzyl ester sulfate (XIV-b):

HPLC shows that the compound (XIV-b) has a purity of 98% and moisture of 1.9%;

m/z: 556 [(M−H$_2$SO$_4$)+H]$^+$, $^1$H NMR (300 MHz, DMSO-d$_6$): δ 1.2 (m, 6H), 1.7 (m, 1H), 3.2 (m, 1H), 3.5 (m, 3H), 3.6 (m, 1H), 3.9 (m, 2H), 4.1 (m, 2H), 4.3 (d, 1H), 5.4 (d, 1H), 5.5 (d, 1H), 5.6 (d, 1H), 6.9 (s, 2H), 7.2 (t, 1H), 7.9 (d, 2H), 8.4 (d, 2H);

Elemental analysis: calculated: C$_{44}$H$_{62}$N$_{10}$O$_{21}$S$_5$, C, 43.06%; H, 5.09%; N, 11.41%; S, 13.06%. Measured: C, 42.33%; H, 5.31%; N, 10.99%; S, 13.31%.

The chemical structural formula of the compound (XIV-b) is as follows:

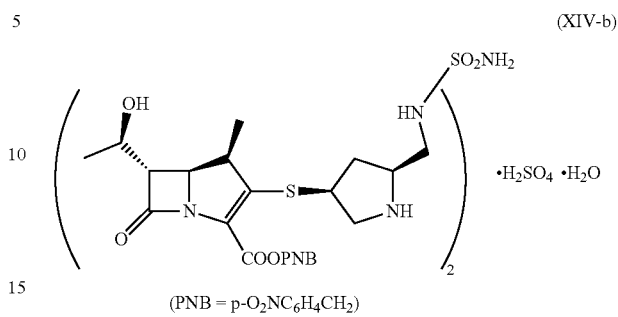

(XIV-b)

(PNB = p-O$_2$NC$_6$H$_4$CH$_2$)

Figure 2:
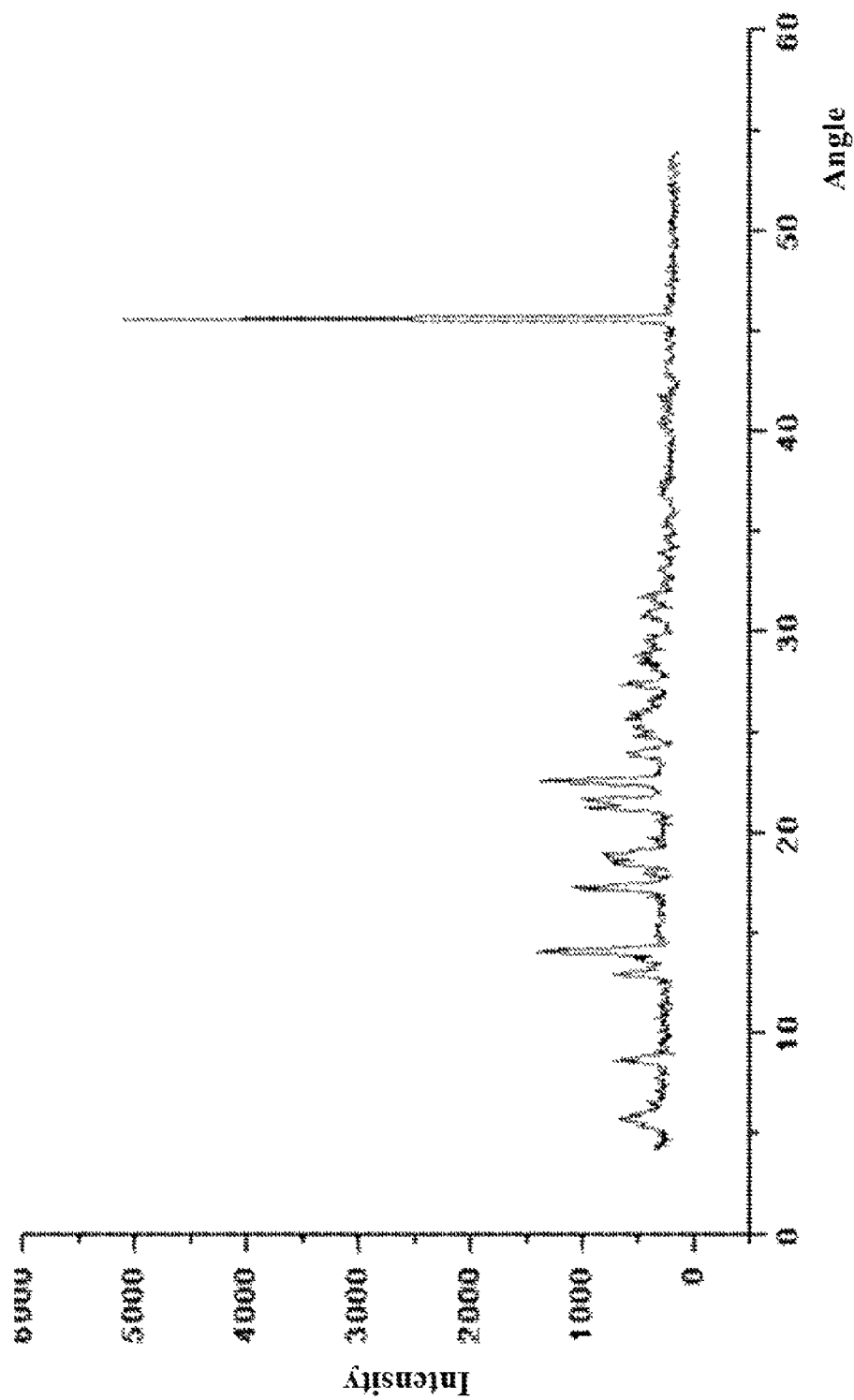
FIG. 2 shows X-ray powder diffraction pattern of the crystal of the compound represented by formula (XIV-b) prepared in Example 2.

The X-ray diffraction pattern of the compound (XIV-b) crystal is shown in FIG. 2, and the specific testing conditions and results are shown in Table 2.

Testing instrument: Innov-X systems BTX-219 X-ray diffractometer.

Testing conditions: target: Cu; 2θ scan at the beginning: 3.000; 2θ scan at the end: 60.000; voltage: 30 KV; current: 330 μA; Ka1=1.54060, Ka2=1.54433, Ka2/Ka1=0.5, Ka=1.54184.

TABLE 2

X-ray diffraction pattern data of the compound (XIV-b)

| NOs | Angles of 2θ | d (Angstrom) values | Intensity countings | Intensities (%) |
|---|---|---|---|---|
| 1 | 12.90 | 6.8571 | 715 | 14.0 |
| 2 | 14.05 | 6.2983 | 1346 | 26.4 |
| 3 | 17.20 | 5.1513 | 1011 | 19.8 |
| 4 | 21.20 | 4.1875 | 963 | 18.9 |
| 5 | 21.65 | 4.1015 | 1003 | 19.7 |
| 6 | 22.50 | 3.9484 | 1378 | 27.0 |
| 7 | 45.55 | 1.9899 | 5104 | 100.0 |

EXAMPLE 3

Synthesis of Compound (XIV-c)

Under the protection of nitrogen, 11.88 g (20 mmol) compound (II) and 9.9 g (40 mmol) compound(XV) were dissolved in 100 ml N,N-dimethylacetamide, cooled to 15° C., and added slowly with 11.1 g (60 mmol) tri-n-butylamine, and then stirred for 3 hours after the completion of addition, then the reaction finished; the reaction mixture was added into 600 ml acetic acid solution with weight percent concentration of 2%, and stirred for 5 hours with the temperature controlled below 40° C., and then filtered and dried, then 11.2 g white crystalline solid compound (XIV-c) was obtained with yield of 90%.

(+)-(4R,5S,6S)-6-[(1R)-1-hydroxyethyl]-4-methyl-7-oxo-3-[[(3S,5S)-5-[(aminosulfonylamino)-methyl]-3-pyrrolidinyl]thio]-1-azabicyclo[3.2.0]hept-2-ene-2-carboxylic acid p-nitrobenzyl ester acetate (XIV-c):

HPLC shows that the compound (XIV-c) has a purity of 95% and moisture of 1.3%;

m/z: 556 [(M−CH$_3$COOH)+H]$^+$, $^1$H NMR (300 MHz, DMSO-d$_6$): δ 1.2 (m, 6H), 1.8 (m, 1H), 2.5 (m, 3H), 3.1 (m, 1H), 3.5 (m, 3H), 3.6 (m, 1H), 4.0 (m, 2H), 4.1 (m, 2H), 4.3 (d, 1H), 5.4 (d, 1H), 5.5 (d, 1H), 5.6 (d, 1H), 6.9 (s, 2H), 7.2 (t, 1H), 7.8 (d, 2H), 8.3 (d, 2H);

Elemental analysis: calculated: $C_{24}H_{35}N_5O_{11}S_2$, C, 45.49%; H, 5.57%; N, 11.05%; S, 10.12%. Measured: C, 46.40%; H, 5.44%; N, 10.97%; S, 9.98%.

The chemical structural formula of the compound (XIV-c) is as follows:

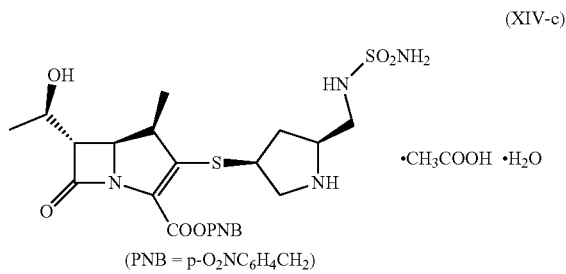

(XIV-c)

(PNB = p-$O_2NC_6H_4CH_2$)

Figure 3:
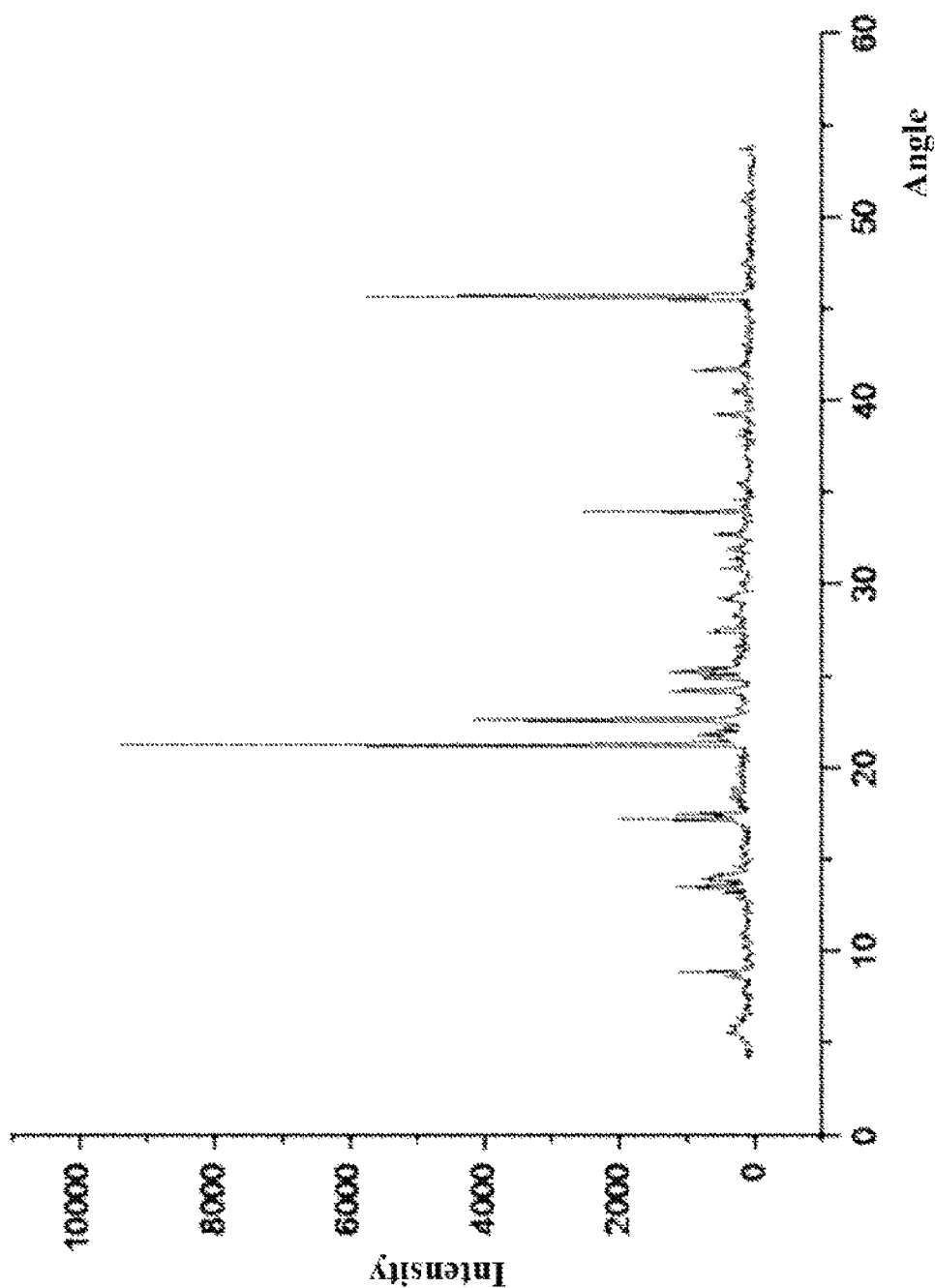
FIG. 3 shows X-ray powder diffraction pattern of the crystal of the compound represented by formula (XIV-c) prepared in Example 3.

The X-ray diffraction pattern of the compound (XIV-c) crystal is shown in FIG. 3, and the specific testing conditions and results are shown in Table 3.

Testing instrument: Innov-X systems BTX-219 X-ray diffractometer.

Testing conditions: target: Cu; 2θ scan at the beginning: 3.000; 2θ scan at the end: 60.000; voltage: 30 KV; current: 330 μA; Ka1=1.54060, Ka2=1.54433, Ka2/Ka1=0.5, Ka=1.54184.

TABLE 3

X-ray diffraction pattern data of the compound (XIV-c)

| NOs | Angles of 2θ | d (Angstrom) values | Intensity countings | Intensities (%) |
|---|---|---|---|---|
| 1 | 8.85 | 9.9839 | 1216 | 24.3 |
| 2 | 13.45 | 6.5779 | 2448 | 49.0 |
| 3 | 17.45 | 5.0780 | 3975 | 79.0 |
| 4 | 21.20 | 4.1875 | 4993 | 100.0 |
| 5 | 22.55 | 3.9398 | 4985 | 99.8 |
| 6 | 24.15 | 3.6823 | 1217 | 24.4 |
| 7 | 25.15 | 3.5381 | 3615 | 72.4 |
| 8 | 27.45 | 3.2466 | 1422 | 28.5 |
| 9 | 33.95 | 2.6384 | 1130 | 22.6 |
| 10 | 39.20 | 2.2963 | 791 | 15.8 |
| 11 | 41.65 | 2.1667 | 759 | 15.2 |
| 12 | 45.60 | 1.9878 | 2713 | 54.3 |

EXAMPLE 4

Synthesis of Compound (XIV-d)

Under the protection of nitrogen, 11.88 g (20 mmol) compound (II) and 4.95 g (20 mmol) compound(XV) were dissolved in 100 ml acetonitrile, cooled to −60° C., and added slowly with 2.3 g (20 mmol) tetramethyl guanidine, and then stirred for 24 hours after the completion of addition, then the reaction finished; the reaction mixture was added into 200 ml phosphoric acid solution with weight percent concentration of 1%, and stirred for 5 hours with the temperature controlled below 10° C., and then filtered and dried, then 1.4 g white crystalline solid compound (XIV-d) was obtained with yield of 95%.

(+)-(4R,5S,6S)-6-[(1R)-1-hydroxyethyl]-4-methyl-7-oxo-3-[[(3S,5S)-5-[(aminosulfonylamino)-methyl]-3-pyrrolidinyl]thio]-1-azabicyclo[3.2.0]hept-2-ene-2-carboxylic acid p-nitrobenzyl ester phosphate (XIV-d):

HPLC shows that the compound (XIV-d) has a purity of 99% and moisture of 1.88%.

m/z: 556 [(M−$H_3PO_4$)+H]$^+$, $^1$H NMR (300 MHz, DMSO-$d_6$): δ 1.4 (m, 6H), 2.4 (m, 1H), 3.3 (m, 1H), 3.8 (m, 3H), 3.9 (m, 1H), 4.2 (m, 2H), 4.3 (m, 2H), 4.4 (d, 1H), 5.6 (d, 1H), 5.7 (d, 1H), 6.0 (d, 1H), 7.1 (s, 2H), 7.5 (t, 1H), 8.1 (d, 2H), 8.6 (d, 2H);

Elemental analysis: calculated: $C_{44}H_{63}N_{10}O_{21}PS_4$, C, 43.06%; H, 5.17%; N, 11.41%; S, 10.45%. Measured: C, 42.28%; H, 5.39%; N, 10.88%; S, 10.48%.

The chemical structural formula of the compound (XIV-d) is as follows:

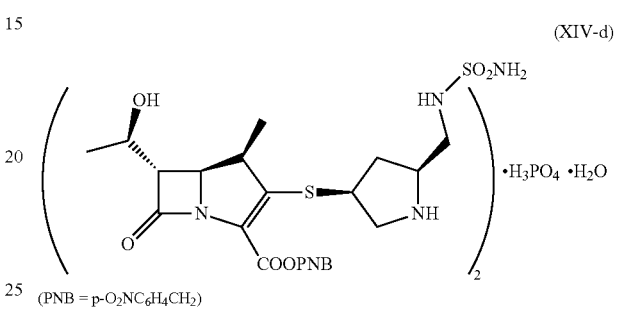

(XIV-d)

(PNB = p-$O_2NC_6H_4CH_2$)

Figure 4:
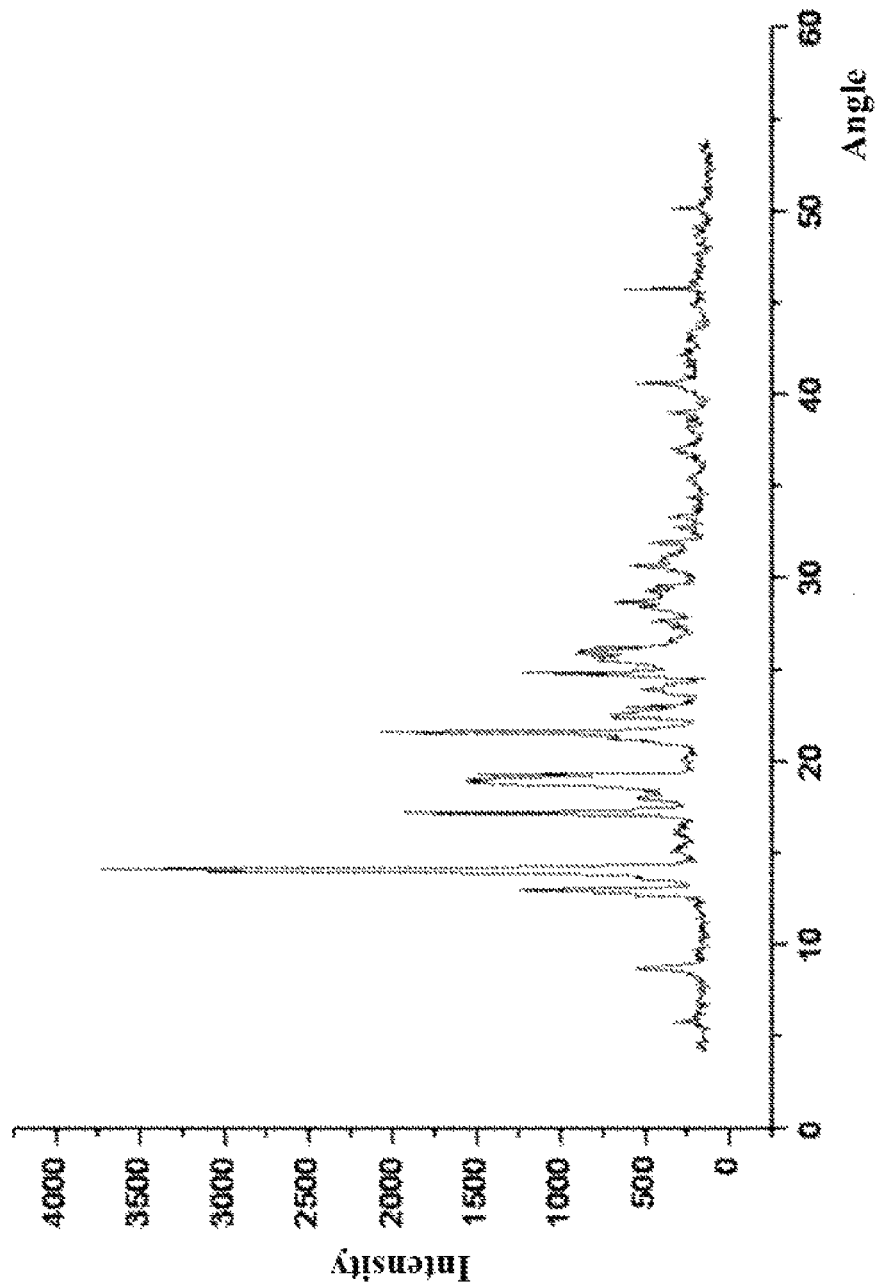
FIG. 4 shows X-ray powder diffraction pattern of the crystal of the compound represented by formula (XIV-d) prepared in Example 4.

The X-ray diffraction pattern of the compound (XIV-d) crystal is shown in FIG. 4, and the specific testing conditions and results are shown in Table 4.

Testing instrument: Innov-X systems BTX-219 X-ray diffractometer.

Testing conditions: target: Cu; 2θ scan at the beginning: 3.000; 2θ scan at the end: 60.000; voltage: 30 KV; current: 330 μA; Ka1=1.54060, Ka2=1.54433, Ka2/Ka1=0.5, Ka=1.54184.

TABLE 4

X-ray diffraction pattern data of the compound (XIV-d)

| NOs | Angles of 2θ | d (Angstrom) values | Intensity countings | Intensities (%) |
|---|---|---|---|---|
| 1 | 12.90 | 6.8571 | 1008 | 28.2 |
| 2 | 14.10 | 6.2761 | 3569 | 100.0 |
| 3 | 17.15 | 5.1662 | 1754 | 49.1 |
| 4 | 18.90 | 4.6916 | 1304 | 36.6 |
| 5 | 19.25 | 4.6071 | 1294 | 36.3 |
| 6 | 21.55 | 4.1203 | 1879 | 52.6 |
| 7 | 24.80 | 3.5872 | 1034 | 29.0 |

EXAMPLE 5

Synthesis of Compound (XIV-e)

Under the protection of nitrogen, 11.88 g (20 mmol) compound (II) and 5.94 g (24 mmol) compound(XV) were dissolved in 100 ml N,N-dimethylformamide, cooled to −20~−25° C., and added slowly with 6.37 g (50 mmol) N,N-diisopropylethylamine, and then stirred for 5 hours after the completion of addition, then the reaction finished; the reaction mixture was added into 500 ml hydrobromic acid aqueous solution with weight percent concentration of 1%, stirred at 0° C. for 30 minutes, and add with 1000 ml isopropanol and stirred for 3 hours with the temperature controlled below 5° C., and then filtered and dried, then 10.6 g white crystalline solid compound (XIV-e) was obtained with yield of 85%.

(+)-(4R,5S,6S)-6-[(1R)-1-hydroxyethyl]-4-methyl-7-oxo-3-[[(3S,5S)-5-[(aminosulfonylamino)-methyl]-3-pyrrolidinyl]thio]-1-azabicyclo[3.2.0]hept-2-ene-2-carboxylic acid p-nitrobenzyl ester hydrobromide (XIV-e).

HPLC shows that the compound (XIV-e) has a purity of 95% and moisture of 2.88%.

m/z: 556 [(M−HBr)+H]$^+$, $^1$H NMR (300 MHz, DMSO-d$_6$): δ 1.2 (m, 6H), 1.6 (m, 1H), 3.1 (m, 1H), 3.3 (m, 3H), 3.5 (m, 1H), 3.7 (m, 2H), 4.0 (m, 2H), 4.3 (d, 1H), 5.2 (d, 1H), 5.3 (d, 1H), 5.4 (d, 1H), 6.8 (s, 2H), 7.0 (t, 1H), 7.7 (d, 2H), 8.2 (d, 2H);

Elemental analysis: calculated: $C_{22}H_{32}BrN_5O_9S_2$, C, 40.37%; H, 4.93%; N, 10.70%; S, 9.80%; measured: C, 41.00%; H, 5.14%; N, 10.80%; S, 9.88%.

The chemical structural formula of the compound (XIV-e) is as follows:

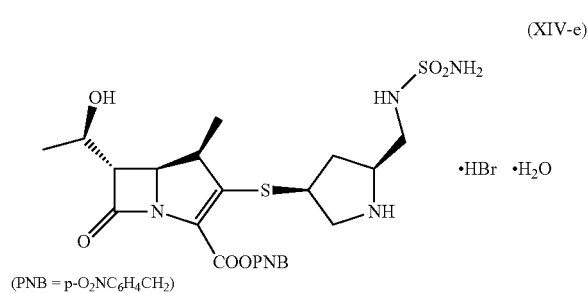

(XIV-e)

(PNB = p-O$_2$NC$_6$H$_4$CH$_2$)

According to the methods of Examples 1-5, when other organic acids or inorganic acids are selected as HX, the following results can be obtained:

f) compound (XIV-f) when HX is nitric acid (HNO$_3$):

m/z: 556 [(M−HNO$_3$)+H]$^+$, $^1$H NMR (300 MHz, DMSO-d$_6$): δ 1.4 (m, 6H), 2.4 (m, 1H), 3.3 (m, 1H), 3.8 (m, 3H), 3.9 (m, 1H), 4.2 (m, 2H), 4.3 (m, 2H), 4.4 (d, 1H), 5.6 (d, 1H), 5.7 (d, 1H), 6.0 (d, 1H), 7.1 (s, 2H), 7.5 (t, 1H), 8.1 (d, 2H), 8.6 (d, 2H);

Elemental analysis: calculated: $C_{22}H_{32}N_6O_{12}S_2$, C, 41.50%; H, 5.07%; N, 13.20%; S, 10.07%. Measured: C, 41.30%; H, 5.14%; N, 12.98%; S, 9.82%.

The chemical structural formula of the compound (XIV-f) is as follows:

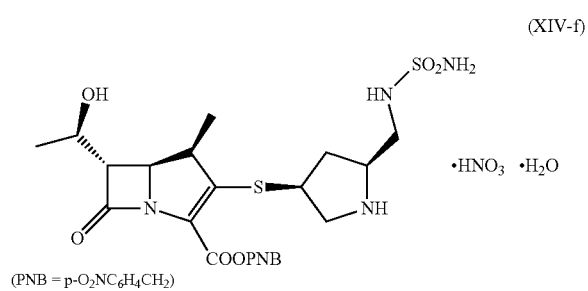

(XIV-f)

(PNB = p-O$_2$NC$_6$H$_4$CH$_2$)

g) compound (XIV-g) when HX is trichloroacetic acid (CCl$_3$COOH):

m/z: 556 [(M−CCl$_3$COOH)+H]$^+$, $^1$H NMR (300 MHz, DMSO-d$_6$): δ 1.2 (m, 6H), 1.6 (m, 1H), 3.1 (m, 1H), 3.3 (m, 3H), 3.5 (m, 1H), 3.7 (m, 2H), 4.0 (m, 2H), 4.3 (d, 1H), 5.2 (d, 1H), 5.3 (d, 1H), 5.4 (d, 1H), 6.8 (s, 2H), 7.0 (t, 1H), 7.7 (d, 2H), 8.2 (d, 2H);

Elemental analysis: calculated: $C_{24}H_{32}Cl_3N_5O_{11}S_2$, C, 39.11%; H, 4.38%; N, 9.50%; S, 8.70%. Measured: C, 40.00%; H, 4.44%; N, 10.00%; S, 8.99%.

The chemical structural formula of the compound (XIV-g) is as follows:

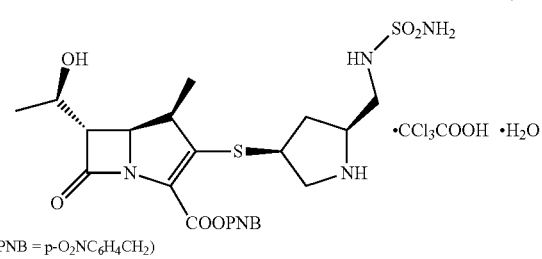

(XIV-g)

(PNB = p-O$_2$NC$_6$H$_4$CH$_2$)

h) compound (XIV-h) when HX is methanesulfonic acid (CH$_4$O$_3$S):

m/z: 556 [(M−CH$_4$O$_3$S)+H]$^+$, $^1$H NMR (300 MHz, DMSO-d$_6$): δ 1.3 (m, 6H), 1.9 (m, 1H), 2.6 (m, 3H), 3.1 (m, 1H), 3.5 (m, 3H), 3.6 (m, 1H), 4.0 (m, 2H), 4.1 (m, 2H), 4.3 (d, 1H), 5.4 (d, 1H), 5.8 (d, 1H), 5.9 (d, 1H), 6.7 (s, 2H), 7.3 (t, 1H), 7.9 (d, 2H), 8.3 (d, 2H);

Elemental analysis: calculated: $C_{23}H_{35}N_5O_{12}S_3$, C, 41.25%; H, 5.27%; N, 10.46%; S, 14.36%. Measured: C, 41.40%; H, 5.54%; N, 10.90%; S, 15.00%.

The chemical structural formula of the compound (XIV-h) is as follows:

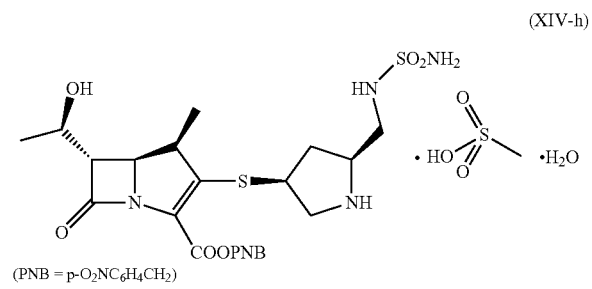

(XIV-h)

(PNB = p-O$_2$NC$_6$H$_4$CH$_2$)

i) compound (XIV-i) when HX is benzenesulfonic acid (C$_6$H$_6$O$_3$S):

m/z: 556 [(M−C$_6$H$_6$O$_3$S)+H]$^+$, $^1$H NMR (300 MHz, DMSO-d$_6$): δ 1.2 (m, 6H), 1.6 (m, 1H), 3.1 (m, 1H), 3.3 (m, 3H), 3.5 (m, 1H), 3.7 (m, 2H), 4.0 (m, 2H), 4.3 (d, 1H), 5.2 (d, 1H), 5.3 (d, 1H), 5.4 (d, 1H), 6.8 (s, 2H), 7.0 (m, 2H), 7.7 (d, 4H), 8.2 (d, 4H);

Elemental analysis: calculated: $C_{28}H_{37}N_5O_{12}S_3$, C, 45.95%; H, 5.10%; N, 9.57%; S, 13.14%. Measured: C, 46.00%; H, 5.12%; N, 10.00%; S, 13.58%.

The chemical structural formula of the compound (XIV-i) is as follows:

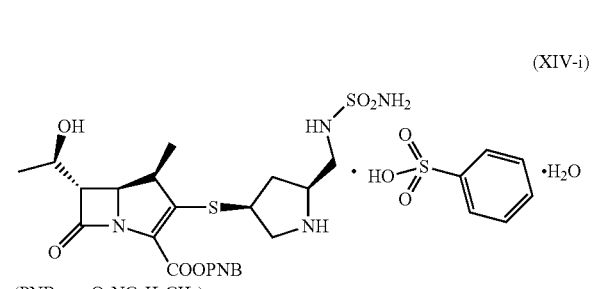

(XIV-i)

(PNB = p-O$_2$NC$_6$H$_4$CH$_2$)

j) compound (XIV-j) when HX is oxalic acid (C$_2$H$_2$O$_4$):

m/z: 556 [(M−C$_2$H$_2$O$_4$)+H]$^+$, $^1$H NMR (300 MHz, DMSO-d$_6$): δ 1.3 (m, 6H), 2.3 (m, 1H), 3.3 (m, 1H), 3.8 (m, 3H), 3.9 (m, 1H), 4.1 (m, 2H), 4.2 (m, 2H), 4.4 (d, 1H), 5.6 (d, 1H), 5.7 (d, 1H), 6.0 (d, 1H), 7.1 (s, 2H), 7.5 (t, 1H), 8.1 (d, 2H), 8.6 (d, 2H);

Elemental analysis: calculated: $C_{46}H_{62}N_{10}O_{21}S_4$, C, 45.31%; H, 5.13%; N, 11.49%; S, 10.52%. Measured: C, 46.01%; H, 5.11%; N, 12.00%; S, 10.58%.

The chemical structural formula of the compound (XIV-j) is as follows:

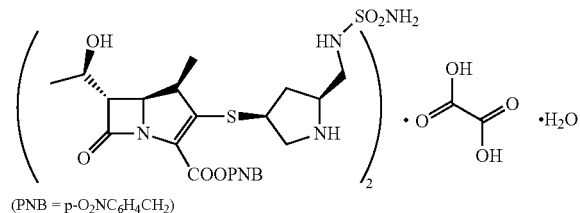

(XIV-j)

(PNB = p-O₂NC₆H₄CH₂)

k) compound (XIV-k) when HX is formic acid ($CH_2O_2$)

m/z: 556 [(M–$CH_2O_2$)+H]⁺, ¹H NMR (300 MHz, DMSO-d₆): δ 1.2 (m, 6H), 1.8 (m, 1H), 2.5 (m, 1H), 3.1 (m, 1H), 3.5 (m, 2H), 3.6 (m, 1H), 4.0 (m, 2H), 4.1 (m, 2H), 4.3 (d, 1H), 5.4 (d, 1H), 5.5 (d, 1H), 5.6 (d, 1H), 6.9 (s, 2H), 7.2 (t, 1H), 7.8 (d, 2H), 8.3 (d, 2H);

Elemental analysis: calculated: $C_{23}H_{33}N_5O_{11}S_2$, C, 44.58%; H, 5.37%; N, 11.30%; S, 10.35%. Measured: C, 45.01%; H, 5.21%; N, 11.330%; S, 10.48%.

The chemical structural formula of the compound (XIV-k) is as follows:

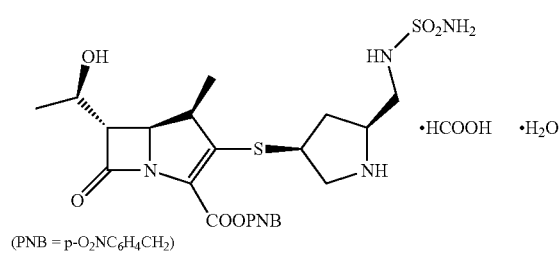

(XIV-k)

(PNB = p-O₂NC₆H₄CH₂)

l) compound (XIV-l) when HX is propionic acid ($C_3H_6O_2$):

m/z: 556 [(M–$C_3H_6O_2$)+H]⁺, ¹H NMR (300 MHz, DMSO-d₆): δ 1.2 (m, 6H), 1.6 (m, 1H), 3.1 (m, 1H), 3.3 (m, 3H), 3.5 (m, 3H), 3.7 (m, 2H), 4.0 (m, 2H), 4.3 (d, 1H), 5.2 (d, 1H), 5.3 (d, 1H), 5.4 (d, 1H), 6.8 (s, 2H), 7.0 (t, 1H), 7.7 (d, 2H), 8.2 (d, 2H);

Elemental analysis: calculated: $C_{25}H_{37}N_5O_{11}S_2$, C, 46.36%; H, 5.76%; N, 10.81%; S, 9.90%. Measured: C, 46.20%; H, 5.94%; N, 10.00%; S, 9.99%.

The chemical structural formula of the compound (XIV-l) is as follows:

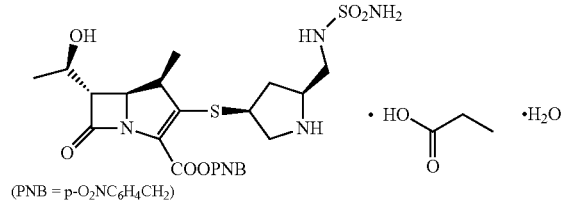

(XIV-l)

(PNB = p-O₂NC₆H₄CH₂)

m) compound (XIV-m) when HX is n-butyric acid ($C_4H_8O_2$):

m/z: 556 [(M–$C_4H_8O_2$)+H]⁺, ¹H NMR (300 MHz, DMSO-d₆): δ 1.2 (m, 6H), 1.6 (m, 1H), 3.1 (m, 1H), 3.3 (m, 3H), 3.5 (m, 3H), 3.6 (m, 2H), 3.7 (m, 2H), 4.0 (m, 2H), 4.3 (d, 1H), 5.2 (d, 1H), 5.3 (d, 1H), 5.4 (d, 1H), 6.8 (s, 2H), 7.0 (t, 1H), 7.7 (d, 2H), 8.2 (d, 2H);

Elemental analysis: calculated: $C_{26}H_{39}N_5O_{11}S_2$, C, 47.19%; H, 5.94%; N, 10.58%; S, 9.69%. Measured: C, 46.80%; H, 5.94%; N, 10.77%; S, 9.88%.

The chemical structural formula of the compound (XIV-m) is as follows:

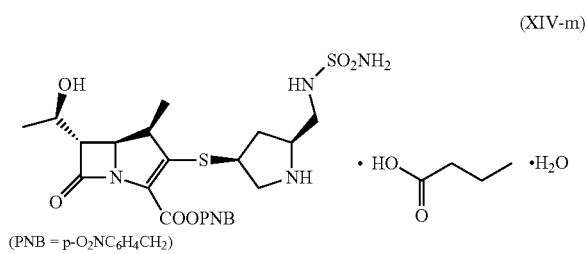

(XIV-m)

(PNB = p-O₂NC₆H₄CH₂)

n) compound (XIV-q) when HX is iso-butyric acid ($C_4H_8O_2$):

m/z: 556 [(M–$C_4H_8O_2$)+H]⁺, ¹H NMR (300 MHz, DMSO-d₆): δ 1.2 (m, 6H), 1.6 (m, 1H), 3.1 (m, 1H), 3.3 (m, 3H), 3.5 (m, 3H), 3.6 (m, 2H), 3.7 (m, 2H), 4.0 (m, 2H), 4.3 (d, 1H), 5.2 (d, 1H), 5.3 (d, 1H), 5.4 (d, 1H), 6.8 (s, 2H), 7.0 (t, 1H), 7.7 (d, 2H), 8.2 (d, 2H);

Elemental analysis: calculated: $C_{26}H_{39}N_5O_{11}S_2$, C, 47.19%; H, 5.94%; N, 10.58%; S, 9.69%. Measured: C, 46.80%; H, 5.94%; N, 10.77%; S, 9.88%.

The chemical structural formula of the compound (XIV-n) is as follows:

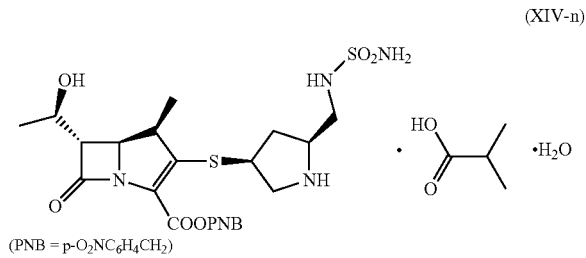

(XIV-n)

(PNB = p-O₂NC₆H₄CH₂)

o) compound (XIV-o) when HX is benzoic acid ($C_7H_6O_2$):

m/z: 556 [(M–$C_7H_6O_2$)+H]⁺, ¹H NMR (300 MHz, DMSO-d₆): δ 1.2 (m, 6H), 1.6 (m, 1H), 3.1 (m, 1H), 3.3 (m, 3H), 3.5 (m, 1H), 3.7 (m, 2H), 4.0 (m, 2H), 4.3 (d, 1H), 5.2 (d, 1H), 5.3 (d, 1H), 5.4 (d, 1H), 6.8 (s, 2H), 7.0 (m, 2H), 7.7 (d, 4H), 8.2 (d, 4H);

Elemental analysis: calculated: $C_{29}H_{37}N_5O_{11}S_2$, C, 50.50%; H, 5.36%; N, 10.07%; S, 9.22%. Measured: C, 50.70%; H, 5.22%; N, 10.00%; S, 9.33%.

The chemical structural formula of the compound (XIV-o) is as follows:

(XIV-o)

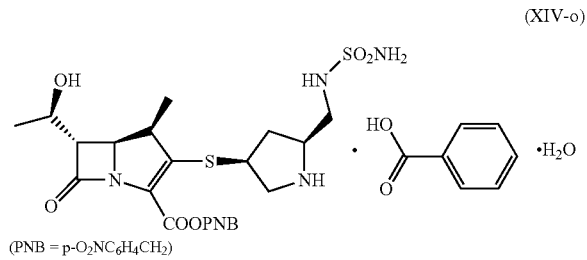

(PNB = p-O₂NC₆H₄CH₂)

p) compound (XIV-p) when HX is maleic acid ($C_4H_4O_4$):
m/z: 556 [(M–$C_4H_4O_4$)+H]⁺, ¹H NMR (300 MHz, DMSO-$d_6$): δ 1.2 (m, 6H), 1.8 (m, 1H), 2.5 (m, 3H), 3.1 (m, 1H), 3.5 (m, 2H), 3.6 (m, 1H), 4.0 (m, 2H), 4.1 (m, 2H), 4.3 (d, 1H), 5.4 (d, 1H), 5.5 (d, 1H), 5.6 (d, 1H), 6.9 (s, 2H), 7.2 (t, 1H), 7.8 (d, 2H), 8.3 (d, 2H);

Elemental analysis: calculated: $C_{48}H_{64}N_{10}O_{21}S_4$, C, 46.29%; H, 5.18%; N, 11.25%; S, 10.30%. Measured: C, 46.01%; H, 5.11%; N, 11.50%; S, 10.48%.

The chemical structural formula of the compound (XIV-p) is as follows:

(XIV-p)

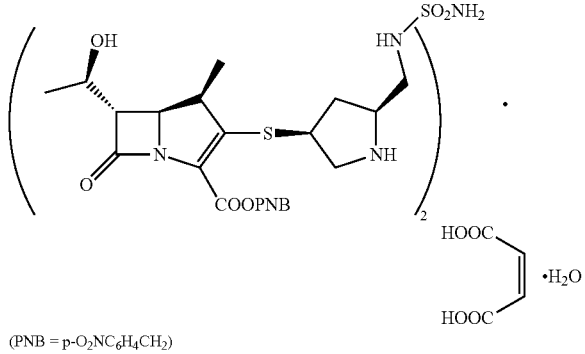

(PNB = p-O₂NC₆H₄CH₂)

r) compound (XIV-q) when HX is succinic acid ($C_4H_6O_4$):
m/z: 556 [(M–$C_4H_4O_4$)+H]⁺, ¹H NMR (300 MHz, DMSO-$d_6$): δ 1.2 (m, 6H), 1.8 (m, 1H), 2.5 (m, 3H), 3.1 (m, 3H), 3.5 (m, 2H), 3.6 (m, 1H), 4.0 (m, 2H), 4.1 (m, 2H), 4.3 (d, 1H), 5.4 (d, 1H), 5.5 (d, 1H), 5.6 (d, 1H), 6.9 (s, 2H), 7.2 (t, 1H), 7.8 (d, 2H), 8.3 (d, 2H);

Elemental analysis: calculated $C_{48}H_{66}N_{10}O_{21}S_4$, C, 46.22%; H, 5.33%; N, 11.23%; S, 10.28%. Measured: C, 46.11%; H, 5.12%; N, 11.40%; S, 10.47%.

The chemical structural formula of the compound (XIV-q) is as follows:

(XIV-q)

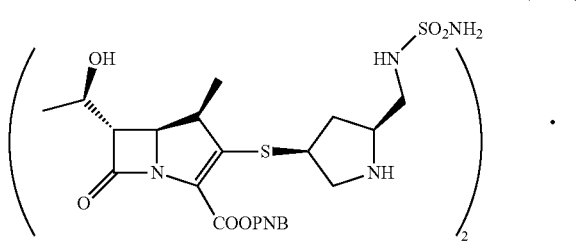

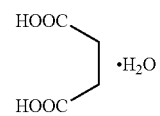

(PNB = p-O₂NC₆H₄CH₂)

r) compound (XIV-r) when HX is fumaric acid ($C_4H_4O_4$):
m/z: 556 [(M–$C_4H_4O_4$)+H]⁺, ¹H NMR (300 MHz, DMSO-$d_6$): δ 1.2 (m, 6H), 1.8 (m, 1H), 2.5 (m, 3H), 3.1 (m, 1H), 3.5 (m, 2H), 3.6 (m, 1H), 4.0 (m, 2H), 4.1 (m, 2H), 4.3 (d, 1H), 5.4 (d, 1H), 5.5 (d, 1H), 5.6 (d, 1H), 6.9 (s, 2H), 7.2 (t, 1H), 7.8 (d, 2H), 8.3 (d, 2H);

Elemental analysis: calculated: $C_{48}H_{64}N_{10}O_{21}S_4$, C, 46.29%; H, 5.18%; N, 11.25%; S, 10.30%. Measured: C, 46.01%; H, 5.11%; N, 11.50%; S, 10.48%.

The chemical structural formula of the compound (XIV-r) is as follows:

(XIV-r)

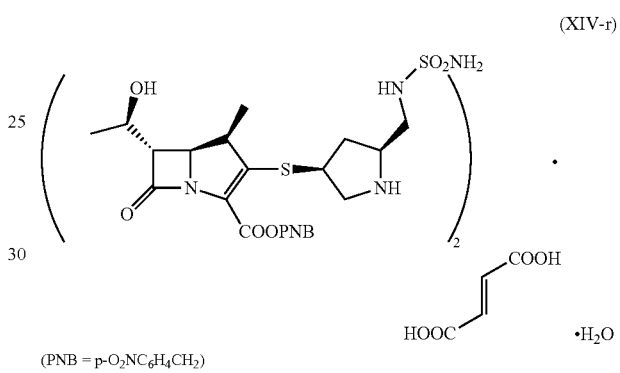

(PNB = p-O₂NC₆H₄CH₂)

s) compound (XIV-s) when HX is lactic acid ($C_3H_6O_3$):
m/z: 556 [(M–$C_3H_6O_3$)+H]⁺, ¹H NMR (300 MHz, DMSO-$d_6$): δ 1.2 (m, 6H), 1.6 (m, 1H), 3.1 (m, 1H), 3.3 (m, 3H), 3.5 (m, 3H), 3.7 (m, 1H), 4.0 (m, 2H), 4.3 (d, 1H), 5.2 (d, 1H), 5.3 (d, 1H), 5.4 (d, 1H), 6.8 (s, 2H), 7.0 (t, 1H), 7.7 (d, 2H), 8.2 (d, 2H);

Elemental analysis: calculated: $C_{25}H_{37}N_5O_{12}S_2$, C, 45.24%; H, 5.62%; N, 10.55%; S, 9.66%. Measured: C, 46.00%; H, 5.84%; N, 10.25%; S, 9.69%.

The chemical structural formula of the compound (XIV-s) is as follows:

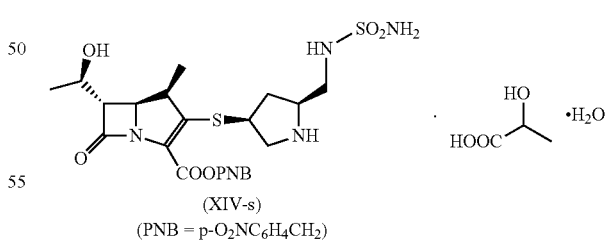

(XIV-s)
(PNB = p-O₂NC₆H₄CH₂)

t) compound (XIV-t) when HX is malic acid ($C_4H_6O_5$):
m/z: 556 [(M–$C_4H_6O_5$)+H]⁺, ¹H NMR (300 MHz, DMSO-$d_6$): δ 1.2 (m, 6H), 1.8 (m, 1H), 2.5 (m, 3H), 3.1 (m, 3H), 3.5 (m, 1H), 3.6 (m, 1H), 4.0 (m, 2H), 4.1 (m, 2H), 4.3 (d, 1H), 5.4 (d, 1H), 5.5 (d, 1H), 5.6 (d, 1H), 6.9 (s, 2H), 7.2 (t, 1H), 7.8 (d, 2H), 8.3 (d, 2H);

Elemental analysis: calculated: $C_{48}H_{66}N_{10}O_{22}S_4$, C, 45.63%; H, 5.27%; N, 11.09%; S, 10.15%. Measured: C, 46.00%; H, 5.32%; N, 11.20%; S, 10.17%.

The chemical structural formula of the compound (XIV-t) is as follows:

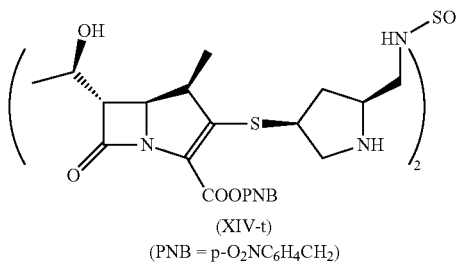

(XIV-t)
(PNB = p-O₂NC₆H₄CH₂)

u) compound (XIV-u) when HX is tartaric acid (C₄H₆O₆):
m/z: 556 [(M–C₄H₆O₆)+H]⁺, ¹H NMR (300 MHz, DMSO-d₆): δ 1.2 (m, 6H), 1.8 (m, 1H), 2.5 (m, 3H), 3.1 (m, 2H), 3.5 (m, 1H), 3.6 (m, 1H), 4.0 (m, 2H), 4.1 (m, 2H), 4.3 (d, 1H), 5.4 (d, 1H), 5.5 (d, 1H), 5.6 (d, 1H), 6.9 (s, 2H), 7.2 (t, 1H), 7.8 (d, 2H), 8.3 (d, 2H);
Elemental analysis: calculated: $C_{48}H_{66}N_{10}O_{23}S_4$, C, 45.06%; H, 5.20%; N, 10.95%; S, 10.03%. Measured: C, 45.00%; H, 5.32%; N, 11.10%; S, 10.07%.

The chemical structural formula of the compound (XIV-u) is as follows:

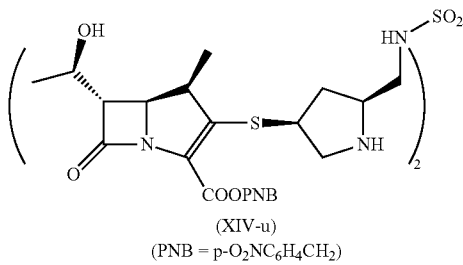

(XIV-u)
(PNB = p-O₂NC₆H₄CH₂)

v) compound (XIV-v) When HX is citric acid (M–C₆H₈O₇):
m/z: 556 [(M–C₆H₈O₇)+H]⁺, ¹H NMR (300 MHz, DMSO-d₆): δ 1.1 (m, 6H), 1.5 (m, 1H), 3.0 (m, 1H), 3.1 (m, 4H), 3.5 (m, 3H), 3.7 (m, 2H), 4.0 (m, 2H), 4.3 (d, 1H), 5.2 (d, 1H), 5.4 (d, 1H), 5.5 (d, 1H), 6.8 (s, 2H), 7.0 (t, 1H), 7.7 (d, 2H), 8.3 (d, 2H);
Elemental analysis: calculated: $C_{50}H_{68}N_{10}O_{24}S_4$, C, 45.45%; H, 5.19%; N, 10.60%; S, 9.71%. Measured: C, 46.00%; H, 5.23%; N, 10.30%; S, 9.97%.

The chemical structural formula of the compound (XIV-v) is as follows:

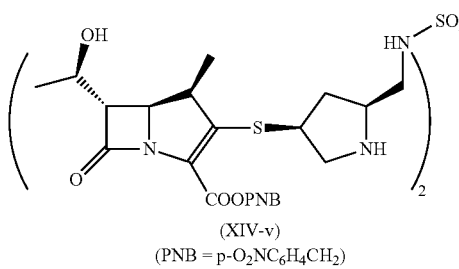

(XIV-v)
(PNB = p-O₂NC₆H₄CH₂)

w) compound (XIV-w) when HX is salicylic acid (C₇H₆O₃)

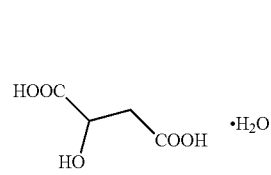
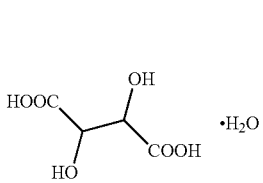

m/z: 556 [(M–C₇H₆O₃)+H]⁺, ¹H NMR (300 MHz, DMSO-d₆): δ 1.2 (m, 6H), 1.6 (m, 1H), 3.1 (m, 1H), 3.3 (m, 3H), 3.5 (m, 1H), 3.7 (m, 1H), 4.0 (m, 2H), 4.3 (d, 1H), 5.2 (d, 1H), 5.3 (d, 1H), 5.4 (d, 1H), 6.8 (s, 2H), 7.0 (m, 2H), 7.7 (d, 4H), 8.2 (d, 4H);
Elemental analysis: calculated: $C_{29}H_{37}N_6O_{12}S_2$, C, 48.94%; H, 5.24%; N, 9.84%; S, 9.01%. Measured: C, 48.99%; H, 5.22%; N, 10.01%; S, 9.23%.

The chemical structural formula of the compound (XIV-w) is as follows:

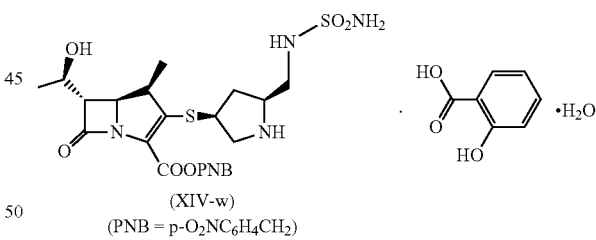
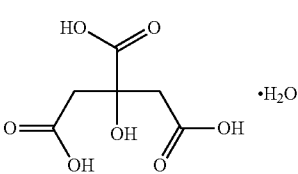

(XIV-w)
(PNB = p-O₂NC₆H₄CH₂)

EXAMPLE 6

Synthesis of Doripenem (I)

6 g compound (XIV-a) was dissolved in a mixed solvent of 90 ml methanol/90 ml water, 6 ml N-methylmorpholine and 1.5 ml acetic acid were used to adjust pH to 6.5-7.5, and 1.4 g Pd/C was added into the mixture, then the mixture was stirred for 1 hour at the temperature of 20~30° C. and hydrogen pressure of 20 atm, and filtered to remove Pd/C, and the filtrate was added into a mixed solvent of 400 ml methanol/1300 ml isopropanol, stirred and crystallized for 4 hours at the temperature of −5° C.~5° C., and then filtered and dried under vacuum, then 3.87 g doripenem was obtained with yield of 89%, HPLC shows that the resulting product has a purity of 97% (m/z 421 [M+H]$^+$).

$^1$H NMR (300 MHz, D$_2$O-d$_2$): δ 1.2 (m, 6H), 1.6 (m, 1H), 2.7 (m, 1H), 3.4 (m, 5H), 3.7 (m, 1H), 3.9 (m, 1H), 4.1 (m, 1H), 4.2 (m, 2H).

EXAMPLE 7

Synthesis of Doripenem (I)

6 g compound (XIV-b) was dissolved in a mixed solvent of 90 ml tetrahydrofuran/90 ml water, 6 ml N-methylmorpholine and 1.5 ml dilute hydrochloric acid were used to adjust pH to 7~8, and 12 g Pd(OH)$_2$/C was added into the mixture, then the mixture was stirred for 5 hours at the temperature of 30~40° C. and hydrogen pressure of 1 atm, and filtered to remove solid impurities, and the filtrate was added into a mixed solvent of 400 ml acetone/1300 ml isopropanol, stirred and crystallized for 4 hours at the temperature of −15° C.~5° C., and then filtered and dried under vacuum, then 3.91 g doripenem was obtained with yield of 90%, HPLC shows that the resulting product has a purity of 98% (m/z 421 [M+H]$^+$).

$^1$H NMR (300 MHz, D$_2$O-d$_2$): δ 1.2 (m, 6H), 1.6 (m, 1H), 2.7 (m, 1H), 3.4 (m, 5H), 3.7 (m, 1H), 3.9 (m, 1H), 4.1 (m, 1H), 4.2 (m, 2H).

EXAMPLE 8

Synthesis of Doripenem (I)

6 g compound (XIV-c) was dissolved in a mixed solvent of 90 ml ethanol/90 ml water, 2 ml 2,6-dimethylpyridine was used to adjust pH to 5~6, and 0.3 g Pt/C was added into the mixture, then the mixture was stirred for 1 hour at the temperature of 20~30° C. and hydrogen pressure of 25 atm, and filtered to remove Pt/C, and the filtrate was added into 1300 ml isopropanol, stirred and crystallized for 4 hours at the temperature of −5° C.~5° C., and then filtered and dried under vacuum, then 4.08 g doripenem was obtained with yield of 97%, HPLC shows that the resulting product has a purity of 96% (m/z 421 [M+H]$^+$).

$^1$H NMR (300 MHz, D$_2$O-d$_2$): δ 1.2 (m, 6H), 1.6 (m, 1H), 2.7 (m, 1H), 3.4 (m, 5H), 3.7 (m, 1H), 3.9 (m, 1H), 4.1 (m, 1H), 4.2 (m, 2H).

EXAMPLE 9

Synthesis of Doripenem (I)

6 g compound (XIV-d) was dissolved in a mixed solvent of 90 ml acetone/60 ml water, 6 ml N-methylmorpholine and 1.3 ml formic acid were used to adjust pH to 4-5, and 1.4 g Pd/C was added into the mixture, then the mixture was stirred for 1 hour at the temperature of 10-20° C. and hydrogen pressure of 20 atm, and filtered to remove Pd/C, and the filtrate was added into a mixed solvent of 400 ml acetone/1300 ml isopropanol, stirred and crystallized for 3 hours at the temperature of −5° C.~5° C., and then filtered and dried under vacuum, then 3.80 g doripenem was obtained with yield of 88%, HPLC shows that the resulting product has a purity of 98% (m/z 421 [M+H]$^+$).

$^1$H NMR (300 MHz, D$_2$O-d$_2$): δ 1.2 (m, 6H), 1.6 (m, 1H), 2.7 (m, 1H), 3.4 (m, 5H), 3.7 (m, 1H), 3.9 (m, 1H), 4.1 (m, 1H), 4.2 (m, 2H).

EXAMPLE 10

Synthesis of Doripenem (I)

6 g compound (XIV-e) was dissolved in a mixed solvent of 60 ml ethanol/600 ml water, 3-morpholinopropanesulfonic acid and sodium hydroxide aqueous solution were used to adjust pH to 7~9, and 1 g Raney Ni was added into the mixture, then the mixture was stirred for 0.5 hour at the temperature of 20~30° C. and hydrogen pressure of 40 atm, and filtered to remove solid impurities, and the filtrate was added into a mixed solvent of 400 ml N,N-dimethylformamide/1300 ml isopropanol, stirred and crystallized for 4 hours at the temperature of −5° C.~5° C., and then filtered and dried under vacuum, then 3.20 g doripenem was obtained with yield of 83%, HPLC shows that the resulting product has a purity of 96% (m/z 421 [M+H]$^+$).

$^1$H NMR (300 MHz, D$_2$O-d$_2$): δ 1.2 (m, 6H), 1.6 (m, 1H), 2.7 (m, 1H), 3.4 (m, 5H), 3.7 (m, 1H), 3.9 (m, 1H), 4.1 (m, 1H), 4.2 (m, 2H).

EXAMPLE 11

Synthesis of Doripenem (I)

6 g compound (XIV-f) was dissolved in a mixed solvent of 600 ml N,N-dimethylformamide/600 ml water, morpholine and acetic acid were used to adjust pH to 6.5-7.5, and 2 g Pd(OH)$_2$/C was added into the mixture, then the mixture was stirred for 1 hour at the temperature of 35~45° C. and hydrogen pressure of 20 atm, and filtered to remove solid impurities, and the filtrate was added into a mixed solvent of 400 ml tetrahydrofuran/1300 ml isopropanol, stirred and crystallized for 5 hours at the temperature of −5° C.~5° C., and then filtered and dried under vacuum, then 4.28 g doripenem was obtained with yield of 84%, HPLC shows that the resulting product has a purity of 98% (m/z 421 [M+H]$^+$).

$^1$H NMR (300 MHz, D$_2$O-d$_2$): δ 1.2 (m, 6H), 1.6 (m, 1H), 2.7 (m, 1H), 3.4 (m, 5H), 3.7 (m, 1H), 3.9 (m, 1H), 4.1 (m, 1H), 4.2 (m, 2H).

EXAMPLE 12

Synthesis of Doripenem (I)

6 g compound (XIV-g) was dissolved in a mixed solvent of 150 ml isopropanol/150 ml water, morpholine and formic acid were used to adjust pH to 6.5~7.5, and 6 g Pd/C was added into the mixture, then the mixture was stirred for 1 hour at the temperature of 30~40° C. and hydrogen pressure of 20 atm, and filtered to remove Pd/C, and the filtrate was added into a mixed solvent of 400 ml tetrahydrofuran/1150 ml isopropanol, stirred and crystallized for 3 hours at the temperature of −5° C.~5° C., and then filtered and dried under vacuum, then 2.82 g doripenem was obtained with yield of 83%, HPLC shows that the resulting product has a purity of 97% (m/z 421 [M+H]$^+$).

$^1$H NMR (300 MHz, D$_2$O-d$_2$): δ 1.2 (m, 6H), 1.6 (m, 1H), 2.7 (m, 1H), 3.4 (m, 5H), 3.7 (m, 1H), 3.9 (m, 1H), 4.1 (m, 1H), 4.2 (m, 2H).

According to the methods of Examples 6-12, when other doripenem intermediates (XIV-h~w) were selected as reactants, the following results can be obtained:

TABLE 5

| Doripenem intermediate | Doripenem (I) (g) | Yield (%) |
|---|---|---|
| XIV-h | 3.24 | 86 |
| XIV-i | 2.86 | 83 |
| XIV-j | 3.32 | 87 |
| XIV-k | 3.58 | 88 |
| XIV-l | 3.32 | 85 |
| XIV-m | 3.44 | 90 |
| XIV-n | 3.36 | 88 |
| XIV-o | 3.03 | 84 |
| XIV-p | 3.55 | 88 |
| XIV-q | 3.50 | 85 |
| XIV-r | 3.02 | 87 |
| XIV-s | 3.25 | 86 |
| XIV-t | 3.07 | 84 |
| XIV-u | 3.10 | 85 |
| XIV-v | 3.20 | 83 |
| XIV-w | 2.21 | 85 |

COMPARATIVE EXAMPLE 1

Synthesis of Doripenem (I)

Doripenem (I) was prepared by referring to "*Organic Process Research & Development*", 2003, volume 7, Pages 846-850:

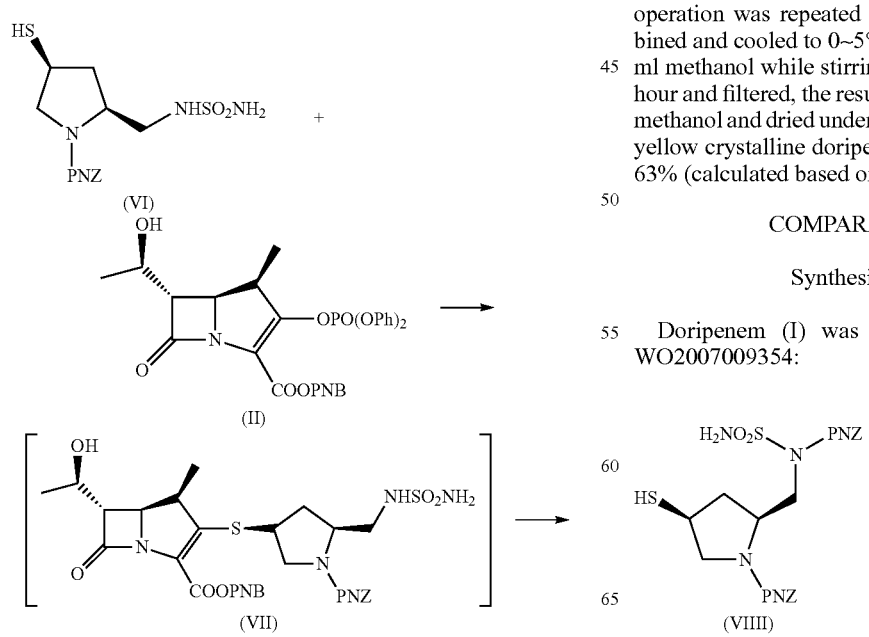

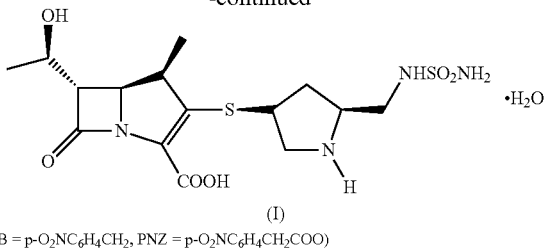

(PNB = p-O$_2$NC$_6$H$_4$CH$_2$, PNZ = p-O$_2$NC$_6$H$_4$CH$_2$COO)

Under the protection of nitrogen, 5.94 g (10 mmol) compound (II) was added into 50 ml dry N,N-dimethylformamide (DMF), and the mixture was cooled to −30° C. while stirring, then added with 11 mmol side-chain compound (VI) and stirred for 10 minutes, then added with 1.80 g (14.2 mmol) N,N-diisopropylethylamine, and then continued to be stirred for 20 hours after completion of addition, and the reaction finished; then the reaction mixture was poured into a mixture of 200 ml ice water and 200 ml ethyl acetate and stirred for 30 minutes, then the ethyl acetate layer was separated, and the water layer extracted twice with ethyl acetate (200 ml each time), the organic layers were combined, and washed with 200 ml dilute hydrochloric acid (0.7%), 200 ml sodium bicarbonate solution (5%) and 200 ml saturated brine once respectively, all of the water layers were combined and back-washed once with 200 ml ethyl acetate, and the organic layers were combined and anhydrous sodium sulfate was added to dry for 2 hours, and then ethyl acetate was recovered under reduced pressure, the resulting product (VII) was directly used for the next step of reaction without further purification.

The above product (VII), 45 ml tetrahydrofuran, 30 ml water, 1.02 g magnesium chloride and 3.8 g palladium/carbon were added into a 1 L hydrogenation reactor. The mixture was vigorously stirred for 2 hours at room temperature and hydrogen pressure of 0.5 MPa, and filtered to remove palladium/carbon, and palladium/carbon was washed with a mixed solvent of 15 ml tetrahydrofuran/8 ml water. The resulting filtrate was added with 0.5 g magnesium chloride and 220 ml tetrahydrofuran and the water layer was separated. The above operation was repeated twice, the water layers were combined and cooled to 0~5° C., the filtrate was added with 150 ml methanol while stirring, and then stirred at −10° C. for 1 hour and filtered, the resulting solid was washed with 100 ml methanol and dried under vacuum, then 2.76 g powder of pale yellow crystalline doripenem (I) was obtained with yield of 63% (calculated based on the compound (II)).

COMPARATIVE EXAMPLE 2

Synthesis of Doripenem (I)

Doripenem (I) was prepared by referring to Patent WO2007009354:

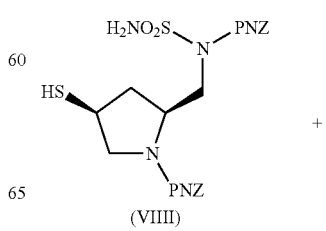

-continued

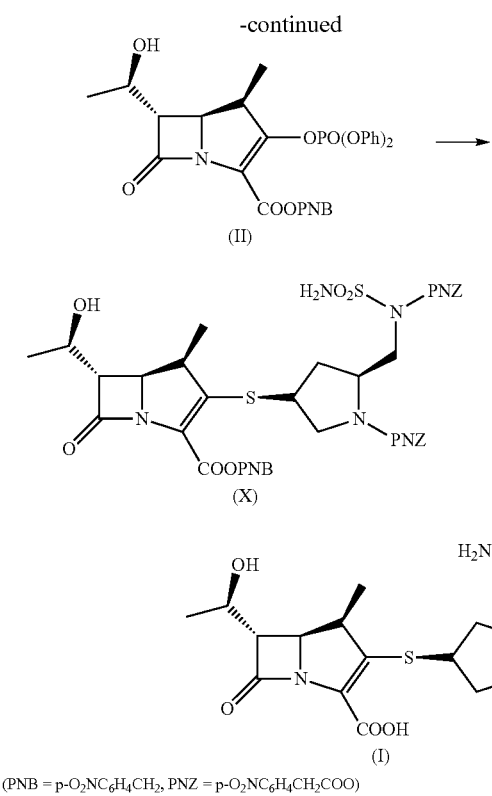

(PNB = p-O₂NC₆H₄CH₂, PNZ = p-O₂NC₆H₄CH₂COO)

Under the protection of nitrogen, 11.88 g (20 mmol) compound (II) and 14.67 g (26 mmol) compound (VIII) were added into 170 ml N,N-dimethylformamide (DMF), and the mixture cooled to 0° C. while stirring, then added with 3.57 g (28 mmol) N,N-diisopropylethylamine, and then continued to be stirred for 2 hours after completion of addition, and the reaction finished; then the reaction mixture was added with 170 ml ethyl acetate and 170 ml 1N hydrochloric acid, and stirred for 5 minutes, the organic layer was separate, and washed with 170 ml 8% sodium bicarbonate aqueous solution and 170 ml saturated brine once respectively, and then anhydrous sodium sulfate was added to dry for 2 hours, and then ethyl acetate was recovered through concentration under reduced pressure, and the resulting concentrate was added with 100 ml toluene and stirred for 2 hours, filtered and dried to obtain 19.7 g pale yellow amorphous compound (X) solid, and the resulting product was directly used for the next step of reaction without further treatment.

19.7 g product (X) prepared above, 350 ml tetrahydrofuran, 230 ml water and 19 g palladium/carbon were added into a 1 L hydrogenation reactor. The mixture was stirred for 4 hours at room temperature and hydrogen pressure of 0.5 MPa, and filtered to remove palladium/carbon, and palladium/carbon was washed with a mixed solvent of 35 ml tetrahydrofuran/23 ml water. The resulting filtrate was added with 2.7 g magnesium chloride and 420 ml tetrahydrofuran, and the water layer was separated. The water phase was cooled to 0~5° C., and added with 750 ml isopropanol while stirring, and then stirred for 2 hours at −10° C. and filtered, the resulting solid was washed with 150 ml acetone and then dried under vacuum, then 4.35 g powder of pale yellow crystalline doripenem (I) was obtained with yield of 51.8% (calculated based on the compound (II)).

COMPARATIVE EXAMPLE 3

Synthesis of Doripenem (I)

Doripenem (I) was prepared by referring to *Chinese Journal of pharmaceuticals*, 2006, Volume 37, No 6, Pages 361-363.

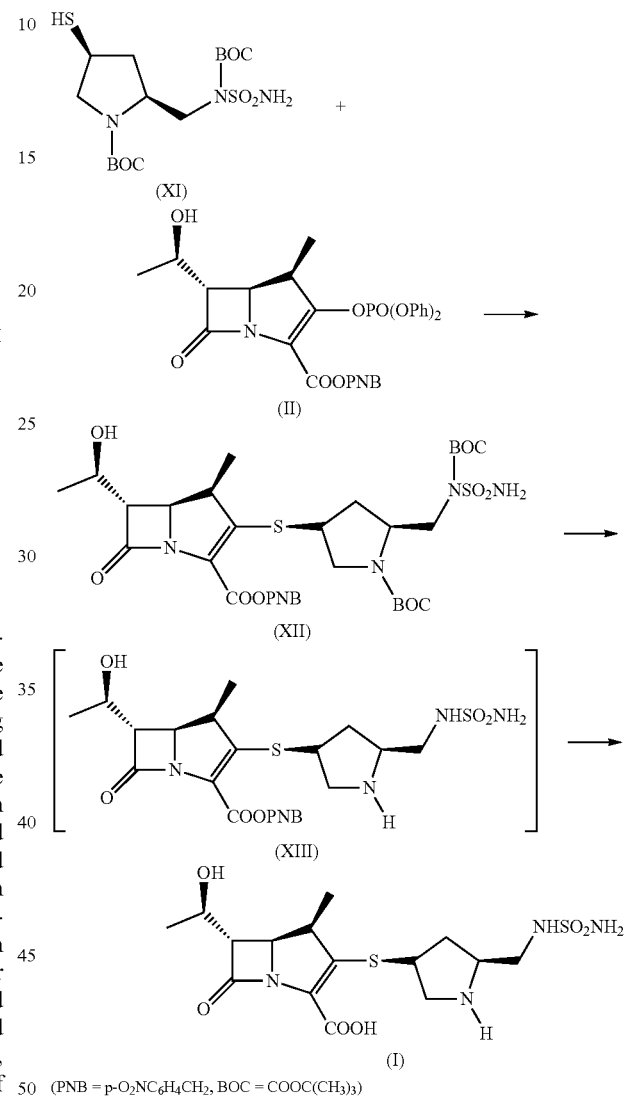

(PNB = p-O₂NC₆H₄CH₂, BOC = COOC(CH₃)₃)

Under the protection of nitrogen, 5.94 g (10 mmol) compound (II) was add into 100 ml dry acetonitrile, and the mixture was cooled to −30° C. while stirring, then added with 4.70 g (11.4 mmol) side-chain compound (XI), and stirred for 10 minutes, then added with 1.58 g (12.4 mmol) N,N-diisopropylethylamine, and then continued to be stirred for 20 hours at the constant temperature after completion of addition, and the reaction finished; then the reaction mixture was poured into a mixture of 200 ml ice water and 200 ml ethyl acetate and stirred for 30 minutes, then the ethyl acetate layer was separated, and the water layer was added with ethyl acetate and extracted twice (200 ml each time), the organic layers were combined, and washed with 200 ml dilute hydrochloric acid (0.7%), 200 ml sodium bicarbonate solution (5%) and 200 ml saturated brine once respectively, all of the water layers were combined and back-washed once with 200 ml ethyl acetate, and the organic layers were combined and anhydrous sodium sulfate was added to dry 2 hours, and ethyl acetate was recovered under reduced pressure, the resulting product (XII) was directly used for the next step of reaction without further purification.

The compound (XII) obtained in the above step was dissolved in 100 ml dichloromethane, the mixture was added with 7.6 ml anisole and 15.5 ml nitromethane, cooled to −60° C., and added with 1 mol/L aluminum chloride in 65 ml nitromethane, then the reaction mixture was heated to −40° C. and stirred for 2 hours, then added with 300 ml ice water, and stirred at 0° C. for 30 minutes and then filtered, the resulting filter cake is the compound (XIII) which was directly used for the next step of reaction.

The above product (XIII), 30 ml tetrahydrofuran, 20 ml water, 1.02 g magnesium chloride and 4 g palladium/carbon were added into a 1 L hydrogenation reactor. The mixture was vigorously stirred for 2 hours at room temperature and hydrogen pressure of 0.5 MPa, and filtered to remove palladium/carbon, and palladium/carbon was washed with a mixed solvent of 15 ml tetrahydrofuran/8 ml water. The filtrate was added with 150 ml tetrahydrofuran and the water layer was separated. The above operation was repeated once, and the water layers were combined and cooled to 0~5° C., the filtrate was added with 150 ml methanol while stirring, and then stirred at −10° C. for 1 hour and filtered, the resulting solid was washed with 100 ml methanol and then dried under vacuum, then 2.63 g powder of yellow crystalline doripenem (I) was obtained with yield of 60% (calculated based on the compound (II)).

When comparing Examples 1-5 and Examples 6-12 with Comparative Examples 1-3, it can be seen that, the monoprotected side-chain compound (XIV) of doripenem prepared in the present invention has better reaction efficiency and higher yield of hydrogenation.

What is claimed is:

1. A process for preparing a doripenem intermediate compound represented by formula (XIV),

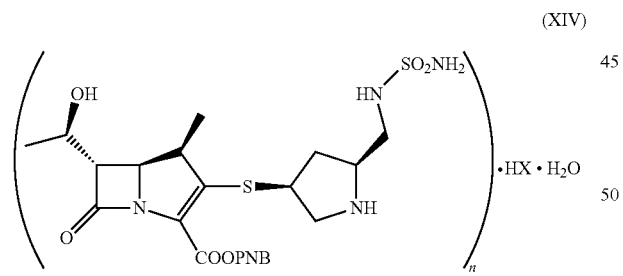

wherein, PNB is p-nitrobenzyl, and HX is selected from hydrochloric acid, hydrobromic acid, nitric acid, acetic acid, formic acid, propionic acid, n-butyric acid, isobutyric acid, trichloroacetic acid, benzoic acid, salicylic acid, lactic acid, sulfuric acid, phosphoric acid, phosphorous acid, oxalic acid, maleic acid, succinic acid, fumaric acid, malic acid, tartaric acid, citric acid; and when HX is a monobasic acid, n=1; and when HX is a polybasic acid, n=2, comprising:

(1-1) reacting a parent nucleus compound (II) of carbapenem antibiotic compounds and a side-chain compound (XV) of doripenem at −60~15° C. in an organic solvent under the action of a base, wherein:

the organic solvent is selected from one or more of acetonitrile, N,N-dimethylformamide, N,N-dimethylacetamide, N,N-diethylformamide and N,N-diethylacetamide;

the base is selected from one or more of triethylamine, N,N-diisopropylethylamine, tetramethyl guanidine and tri-n-butylamine, a molar ratio of the parent nucleus compound (II) of carbapenem antibiotic compounds, the side-chain compound (XV) of doripenem to the base is 1:1~2:1~3;

a reaction concentration calculated based on the parent nucleus compound (II) is 0.01~2 mol/L; and a reaction time is 3-24 hours;

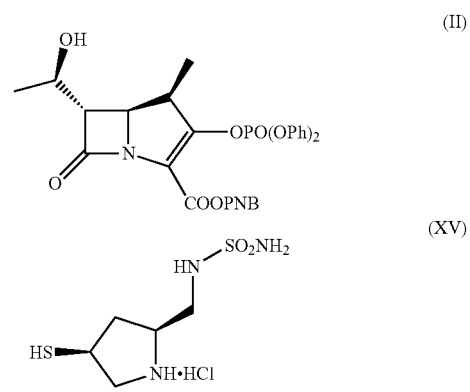

and (1-2) reacting a reaction mixture or product obtained in act (1-1) with a water solution containing HX at −15~40° C. to obtain the doripenem intermediate compound represented by formula (XIV), wherein:

a molar ratio of HX to the parent nucleus compound (II) in act (1-1) is 1~10:1;

a weight percent concentration of the water solution containing HX is 0.01%~1%; and a reaction time is 3-36 hours,

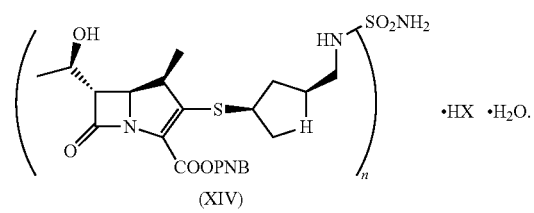

2. The process according to claim 1, wherein the organic solvent is N,N-dimethylformamide and/or acetonitrile.

3. The process according to claim 1, wherein the base is triethylamine and/or N,N-diisopropylethylamine.

4. The process according to claim 1, wherein in act (1-1), the reaction temperature is −35~−15° C.;

the molar ratio of the parent nucleus compound (II) of carbapenem antibiotic compounds, the side-chain compound (XV) of doripenem to the base is 1:1.2:2.5;

the reaction concentration calculated based on the parent nucleus compound (II) is 0.2 mol/L; and the reaction time is 3-5 hours.

5. The process according to claim 1, wherein in act (1-2), the molar ratio of HX to the parent nucleus compound (II) in act (1-1) is 5~6:1;

the weight percent concentration of the water solution containing HX is 0.5%~1%;
the reaction temperature is 0~10° C.; and
the reaction time is 5~6 hours.

6. The process according to claim 1, wherein after act (1-2) the process further comprising:
(1-3) adding a second organic solvent, stirring and washing to perform purification, wherein:
the second organic solvent is selected from one or more of methanol, ethanol, tetrahydrofuran, isopropanol, acetonitrile, N,N-dimethylformamide, N,N-dimethylacetamide, N,N-diethylformamide, N,N-diethylacetamide, acetone, methyl acetate, ethyl acetate, dichloromethane, methyl tert-butyl ether, chloroform and toluene; and
a volume of the second organic solvent is 1~10 times a volume of the organic solvent used in act (1-1).

7. The process according to claim 6, wherein the volume of the second organic solvent is 1~3 times the volume of the organic solvent used in act (1-1).

8. A process for preparing doripenem represented by formula (I), comprising:
catalyzing and hydrogenating the doripenem intermediate compound according to claim 1 in a solvent under the action of a catalyst to obtain the doripenem represented by formula (I),

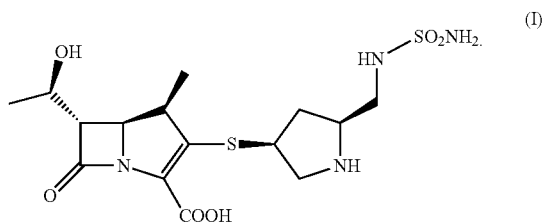 [SMILES: C[C@@H](O)[C@H]1C(=O)N2C(C(=O)O)=C(S[C@@H]3CN[C@H](CNS(N)(=O)=O)C3)[C@H](C)[C@H]12]

wherein the solvent is a mixed solvent of organic solvent/water; the organic solvent is selected from one or more of methanol, tetrahydrofuran, ethanol, N,N-dimethylformamide, acetone and isopropanol; and
the catalyst is selected from one or more of Pd/C, Pd(OH)$_2$/C, Pt/C and Raney Ni.

9. The process according to claim 8, wherein the solvent is a mixed solvent of tetrahydrofuran/water; a volume of tetrahydrofuran, a volume of water and a mass of the doripenem intermediate compound (XIV) are in a ratio of 10~100 ml:10~100 ml:1 g.

10. The process according to claim 9, wherein the volume of tetrahydrofuran, the volume of water and the mass of the doripenem intermediate compound (XIV) are in a ratio of 15 ml:15 ml:1 g.

11. The process according to claim 8, wherein the catalyst is Pd/C; and a mass ratio of Pd/C to the doripenem intermediate compound (XIV) is 0.05~2:1.

12. The process according to claim 11, wherein the mass ratio of Pd/C to the doripenem intermediate compound (XIV) is 0.25:1.

13. The process according to claim 8, wherein the catalyzing and hydrogenating is performed at a hydrogen pressure of 1~40 atm.

14. The process according to claim 8, wherein the catalyzing and hydrogenating is performed at a hydrogen pressure of 20~30 atm.

15. The process according to claim 8, wherein the catalyzing and hydrogenating is performed at a temperature of 0~45° C.

16. The process according to claim 8, wherein the catalyzing and hydrogenating is performed at a temperature of 20~30° C.

17. The process according to claim 8, wherein the catalyzing and hydrogenating is performed at a pH of 4~9.

18. The process according to claim 17, wherein the pH is adjusted by a buffer system, and the buffer system is selected from one or more of N-methyl morpholine/acetic acid, N-methyl morpholine/hydrochloric acid, N-methyl morpholine/formic acid, 2,6-dimethyl pyridine, 3-morpholinopropanesulfonic acid/sodium hydroxide, sodium bicarbonate, morpholine/acetic acid, morpholine/hydrochloric acid, morpholine/formic acid, and potassium dihydrogen phosphate/dipotassium hydrogen phosphate.

19. The process according to claim 8, wherein the catalyzing and hydrogenating is performed at a pH of 6.5~7.5.

20. The process according to claim 19, wherein the pH is adjusted by a buffer system, and the buffer system is selected from one or more of N-methyl morpholine/acetic acid, N-methyl morpholine/hydrochloric acid, N-methyl morpholine/formic acid, 2,6-dimethyl pyridine, 3-morpholinopropanesulfonic acid/sodium hydroxide, sodium bicarbonate, morpholine/acetic acid, morpholine/hydrochloric acid, morpholine/formic acid, and potassium dihydrogen phosphate/dipotassium hydrogen phosphate.

21. The process according to claim 18, wherein the buffer system is N-methyl morpholine/acetic acid and/or 2,6-dimethyl pyridine.

22. The process according to claim 17, wherein the pH is adjusted by N-methyl morpholine/acetic acid, a volume of N-methyl morpholine, a volume of acetic acid and a mass of the doripenem intermediate compound represented by formula (XIV) are in a ratio of 1-5 ml:0.05-2 ml:1 g; or
the pH is adjusted by 2,6-dimethyl pyridine, a volume of 2,6-dimethyl pyridine and the mass of the doripenem intermediate compound represented by formula (XIV) are in a ratio of 0.05~1 ml:1 g.

23. The process according to claim 19, wherein the pH is adjusted by N-methyl morpholine/acetic acid, a volume of N-methyl morpholine, a volume of acetic acid and a mass of the doripenem intermediate compound represented by formula (XIV) are in a ratio of 1~5 ml:0.05-2 ml:1 g; or
the pH is adjusted by 2,6-dimethyl pyridine, a volume of 2,6-dimethyl pyridine and the mass of the doripenem intermediate compound represented by formula (XIV) are in a ratio of 0.05~1 ml:1 g.

24. The process according to claim 22, wherein the volume of N-methyl morpholine, the volume of acetic acid and the mass of the doripenem intermediate compound represented by formula (XIV) are in a ratio of 1 ml:0.25 ml:1 g.

25. The process according to claim 22, wherein the volume of 2,6-dimethyl pyridine and the mass of the doripenem intermediate compound represented by formula (XIV) are in a ratio of 0.33 ml:1 g.

26. The process according to claim 8, the process further comprising:
after being catalyzed and hydrogenated, adding a water-miscible organic solvent to the obtained hydrogenated solution to precipitate a crystal of doripenem (I);
wherein the water-miscible organic solvent is selected from one or more of methanol, isopropanol, acetone, N,N-dimethylformamide, ethanol and tetrahydrofuran.

27. The process according to claim 26, wherein the water-miscible organic solvent is methanol/isopropanol, a volume of methanol, a volume of isopropanol and a mass of the doripenem intermediate compound (XIV) are in a ratio of 30~100 ml:100-300 ml:1 g; or the water-miscible organic solvent is acetone/isopropanol, wherein a volume of acetone, a volume of isopropanol and the mass of the doripenem intermediate compound (XIV) are in a ratio of 20~100 ml:100-300 ml:1 g.

28. The process according to claim 27, wherein the volume of methanol, the volume of isopropanol and the mass of the doripenem intermediate compound (XIV) are in a ratio of 60 ml:225 ml:1 g.

29. The process according to claim 27, wherein the volume of acetone, the volume of isopropanol and the mass of the doripenem intermediate compound (XIV) are in a ratio of 60 ml:225 ml:1 g.

30. The process according to claim 26, wherein the crystallization temperature of doripenem (I) is −15~5° C.

31. The process according to claim 26, wherein the crystallization temperature of doripenem (I) is −5~5° C.

* * * * *